(12) United States Patent
Hirose et al.

(10) Patent No.: US 11,986,239 B2
(45) Date of Patent: May 21, 2024

(54) OPHTHALMOLOGIC APPARATUS AND METHOD OF CONTROLLING THE SAME

(71) Applicant: TOPCON CORPORATION, Tokyo (JP)

(72) Inventors: Ryoichi Hirose, Tokyo (JP); Manabu Sakaihara, Tokyo (JP); Tatsuo Yamaguchi, Warabi (JP)

(73) Assignee: TOPCON CORPORATION, Tokyo (JP)

( * ) Notice: Subject to any disclaimer, the term of this patent is extended or adjusted under 35 U.S.C. 154(b) by 891 days.

(21) Appl. No.: 17/008,678

(22) Filed: Sep. 1, 2020

(65) Prior Publication Data

US 2020/0397282 A1 Dec. 24, 2020

Related U.S. Application Data

(63) Continuation of application No. PCT/JP2019/022665, filed on Jun. 7, 2019.

(30) Foreign Application Priority Data

Aug. 29, 2018 (JP) .................. 2018-160419

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0008* (2013.01); *A61B 3/103* (2013.01); *A61B 3/12* (2013.01)

(58) Field of Classification Search
CPC ....... A61B 3/0008; A61B 3/102; A61B 3/103; A61B 3/12
See application file for complete search history.

(56) References Cited

U.S. PATENT DOCUMENTS

2011/0234975 A1 9/2011 Hirose
2013/0010262 A1 1/2013 Sato et al.
(Continued)

FOREIGN PATENT DOCUMENTS

EP 3335622 A2 6/2018
JP 2010-151704 A 7/2010
(Continued)

OTHER PUBLICATIONS

Office Action dated Jan. 11, 2022, in corresponding Japanese patent Application No. 2020-540077, 14 pages.
(Continued)

*Primary Examiner* — Jack Dinh
(74) *Attorney, Agent, or Firm* — XSENSUS LLP

(57) ABSTRACT

An ophthalmologic apparatus includes an fixation projection system, an interference optical system, and a controller. The fixation projection system is configured to project fixation light flux onto a fundus of a subject's eye. The interference optical system includes an optical scanner and is configured to split light from light source into measurement light and reference light, to irradiate the subject' eye with the measurement light deflected by the optical scanner, and to detect interference light between returning light of the measurement light from the subject's eye and the reference light. The controller is configured to perform OCT measurement on a first scan region and a second scan region, which are different from each other in the subject's eye, by controlling the interference optical system in a state where a projected position of the fixation light flux on the fundus is fixed.

12 Claims, 10 Drawing Sheets

(51) Int. Cl.
  *A61B 3/103* (2006.01)
  *A61B 3/12* (2006.01)

(56) References Cited

U.S. PATENT DOCUMENTS

| | | |
|---|---|---|
| 2013/0258286 A1 | 10/2013 | Iwase et al. |
| 2016/0206193 A1 | 7/2016 | Schmoll et al. |
| 2016/0374547 A1 | 12/2016 | Tanaka et al. |
| 2017/0105618 A1 | 4/2017 | Schmoll et al. |
| 2018/0160897 A1 | 6/2018 | Shimozato et al. |
| 2021/0007601 A1 | 1/2021 | Schmoll et al. |

FOREIGN PATENT DOCUMENTS

| | | |
|---|---|---|
| JP | 2011-214969 A | 10/2011 |
| JP | 2013-081763 A | 5/2013 |
| JP | 2015-513110 A | 4/2015 |
| JP | 2017-006436 A | 1/2017 |
| JP | 2017-522066 A | 8/2017 |
| JP | 2017-195944 A | 11/2017 |
| JP | 2018-094222 A | 6/2018 |
| JP | 2018-114230 A | 7/2018 |
| WO | 2014/084139 A1 | 6/2014 |

OTHER PUBLICATIONS

Japanese Office Action dated Jun. 7, 2022, in corresponding Japanese Patent Application No. 2020-540077, 15 pp.

International Search Report and Written Opinion dated Aug. 13, 2019 for PCT/JP2019/022665 filed on Jun. 7, 2019, 10 pages including English Translation of the International Search Report.

Drexler W. and Fujimoto, J.G., "Optical Coherence Tomography: Technology and Applications" Second Edition, Springer International Publishing, 2015, 21 pages.

Klein, T., and Huber, R., "High-speed OCT light sources and systems," Biomedical Optics Express, vol. 8, No. 2, Feb. 1, 2017, pp. 828-859.

Kolb, J.P., et al., "Ultra-widefield retinal MHz-OCT imaging with up to 100 degrees viewing angle," Biomedical Optics Express, vol. 6, No. 5, May 1, 2015, pp. 1534-1552.

Extended EP Search Report issued for corresponding European Patent Application No. 19853334.1, dated Apr. 4, 2022.

Office Action dated Oct. 24, 2023 in Japanese Patent Application No. 2022-160113, 12 pages.

Japanese Office Action issued Feb. 20, 2024, in corresponding Japanese Patent Application No. 2022-160113, 13 pages.

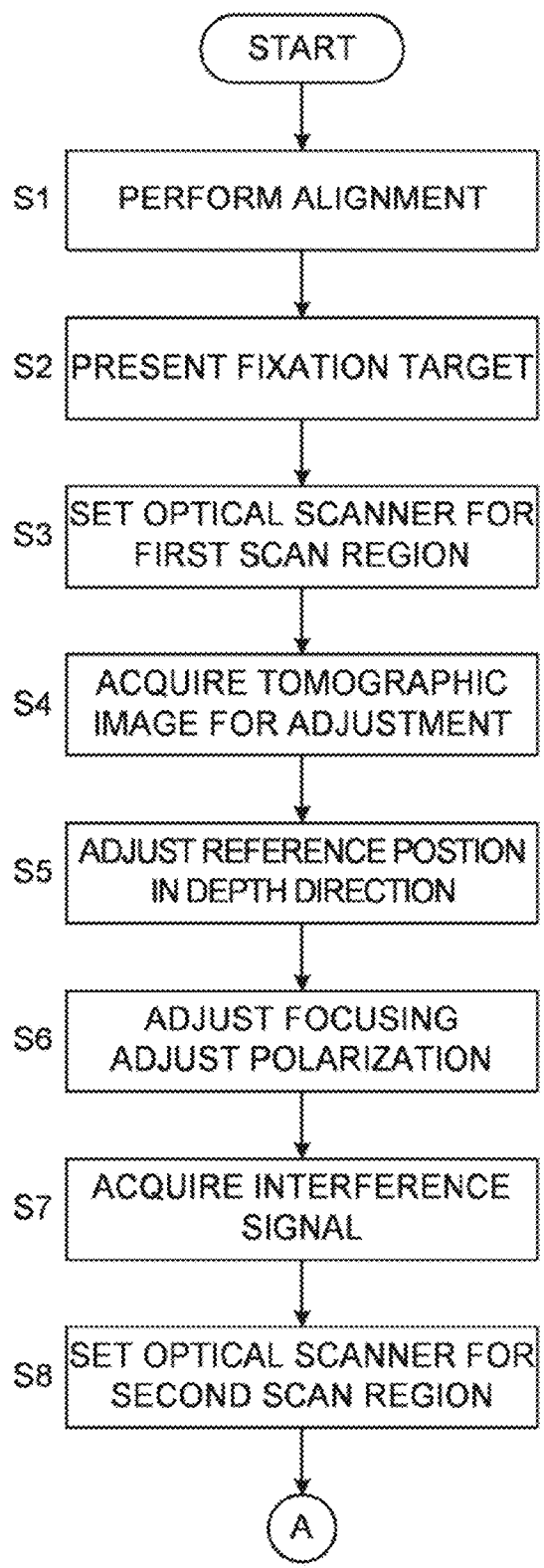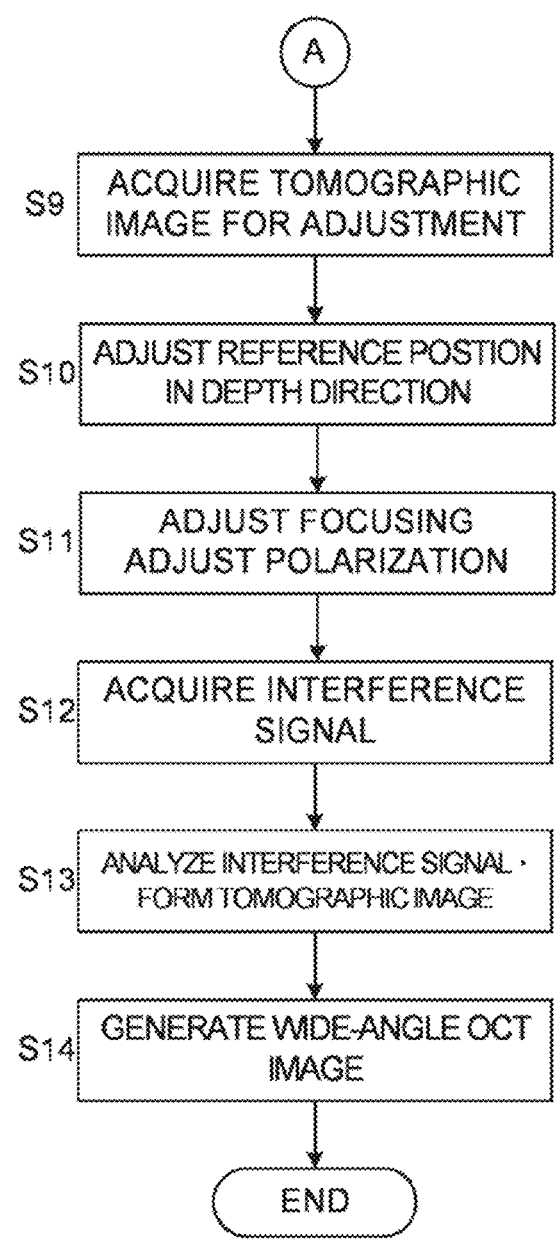
FIG. 7

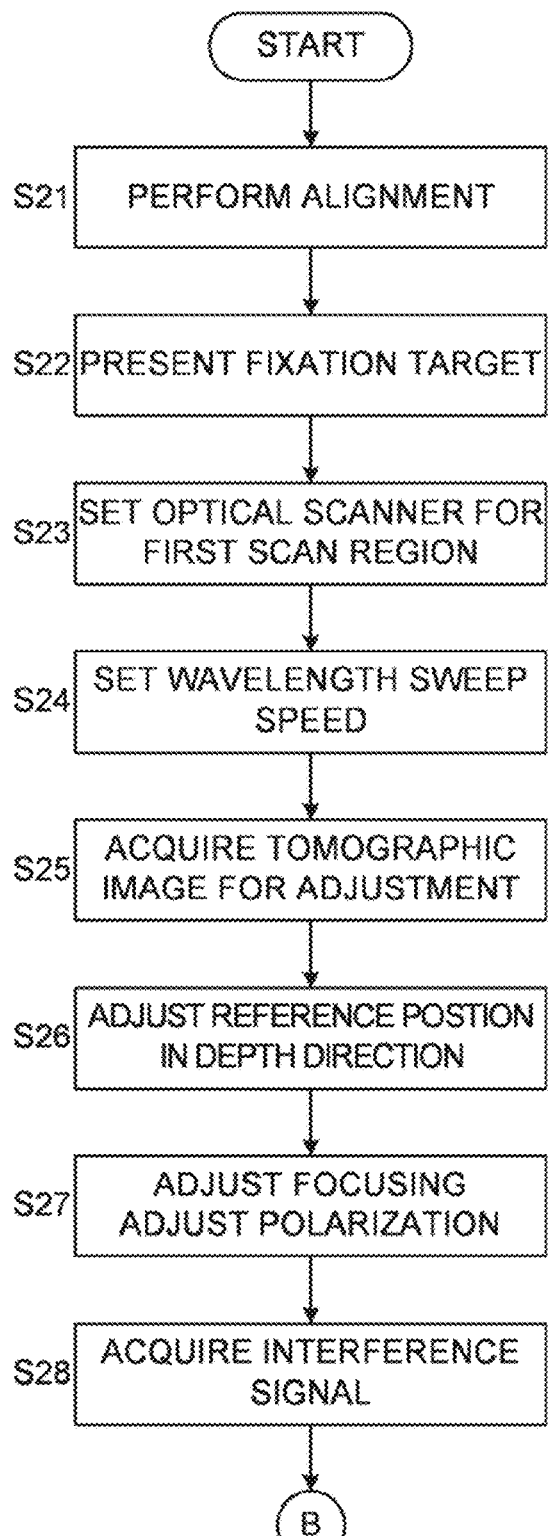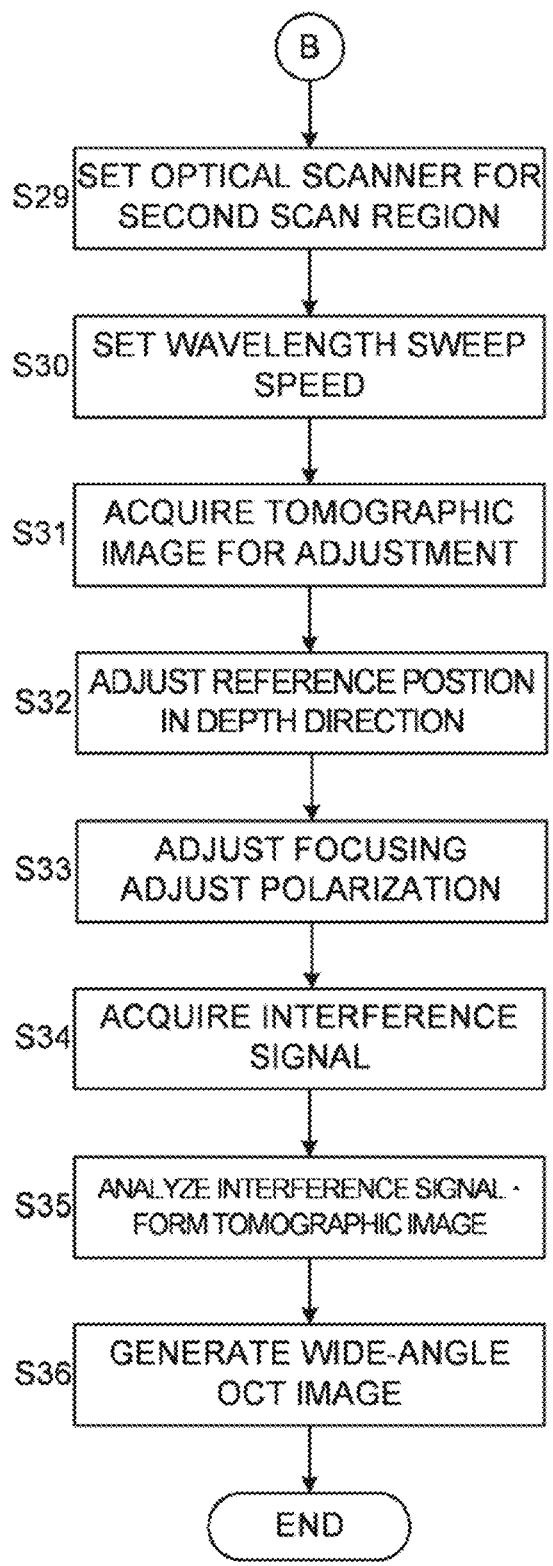
FIG. 8

OPHTHALMOLOGIC APPARATUS AND METHOD OF CONTROLLING THE SAME

CROSS-REFERENCE TO RELATED APPLICATIONS

The present application is a continuation application of International Patent Application No. PCT/JP2019/022665, filed Jun. 7, 2019, which claims priority to Japanese Patent Application No. 2018-160419, filed Aug. 29, 2018. The contents of these applications are incorporated herein by reference in their entirety.

FIELD

The disclosure relates to an ophthalmologic apparatus and a method of controlling the same.

BACKGROUND

In recent years, attention has been drawn to optical coherence tomography (OCT) which is used to measure the morphology of an object to be measured or to image using light beam emitted from a laser light source or the like. Since OCT does not have invasiveness to human body as X-ray CT (Computed Tomography) does, development of application of OCT in medical field and biology field is particularly expected. For example, in the ophthalmologic field, apparatuses for forming images of the fundus or the cornea have been in practical use. Such apparatuses using OCT (OCT apparatuses) can be used to observe or measure a variety of sites (fundus, anterior segment) of a subject's eye. In addition, because of the ability to acquire high precision images, the OCT apparatuses are applied to the diagnosis of various eye diseases.

In measurement (imaging) using OCT, high speed is desired to prevent deterioration of image quality due to fixation disparity during measurement. High-speed OCT measurement is also effective for acquiring high-quality OCT angiography (OCTA) images.

For example, spectral domain OCT (SD-OCT), swept source OCT (SS-OCT), and the like have been proposed as a method for realizing OCT. The spectral domain OCT scans A lines of the object at one time using broadband light and acquires information in a depth direction of the object by dispersing interference light and detecting the spectral distribution. The swept source OCT scans A lines of the object by sweeping within a predetermined wavelength range using a wavelength sweep light source to change a wavelength of measurement light, and acquires information in the depth direction of the object based on the interference spectrum distribution corresponding to the A line on the basis of the sequentially detected interference light. In the spectral domain OCT, the measurement speed of the A scan is limited by the data transfer speed of the image sensor, etc., whereas in the swept source OCT, it is limited by the wavelength sweep speed of the light source. Thus, the swept source OCT is often used to speed up OCT measurements. On the other hand, the demand for speeding up OCT measurements using spectral domain OCT is still high.

For example, "High-speed OCT light sources and systems [Invited]" (T. Klein and R. Huber, Biomedical Optics Express, U.S.A., Jan. 13, 2017, Vol. 8, No. 2, pp. 823-859) discloses a method of performing OCT measurement using the swept source OCT. For example, "Ultra-widefield retinal MHz-OCT imaging with up to 100 degrees viewing angle" (J. P. Kolb et al., Biomedical Optics Express, U.S.A., Apr. 2, 2015, Vol. 6, No. 5, pp. 1534-1552) discloses a method of performing wide-angle OCT measurement on the fundus.

SUMMARY

One aspect of some embodiments is an ophthalmologic apparatus including: a fixation projection system configured to project fixation light flux onto a fundus of a subject's eye; an interference optical system including an optical scanner and configured to split light from light source into measurement light and reference light, to irradiate the subject's eye with the measurement light deflected by the optical scanner, and to detect interference light between returning light of the measurement light from the subject's eye and the reference light; and a controller configured to perform OCT measurement on a first scan region and a second scan region, which are different from each other in the subject's eye, by controlling the interference optical system in a state where a projected position of the fixation light flux on the fundus is fixed.

Another aspect of some embodiments is a method of controlling an ophthalmologic apparatus including: a fixation projection system configured to project fixation light flux onto a fundus of a subject's eye; and an interference optical system including an optical scanner and configured to split light from light source into measurement light and reference light, to irradiate the subject's eye with the measurement light deflected by the optical scanner, and to detect interference light between returning light of the measurement light from the subject's eye and the reference light. The method includes: a first measurement step of performing OCT measurement on a first scan region in the subject's eye by controlling the interference optical system, in a state where the fixation light flux is projected onto the fundus; and a second measurement step of performing OCT measurement on a second scan region in the subject's eye, the second scan region being different from the first scan region, by controlling the interference optical system, in a state where a fixation position in the first measurement step is fixed.

BRIEF EXPLANATION OF THE DRAWING

FIG. 7 is a flowchart illustrating an example of the operation of the ophthalmologic apparatus according to the embodiments.

FIG. 8 is a flowchart illustrating an example of the operation of the ophthalmologic apparatus according to the embodiments.

DETAILED DESCRIPTION

Figure 1:
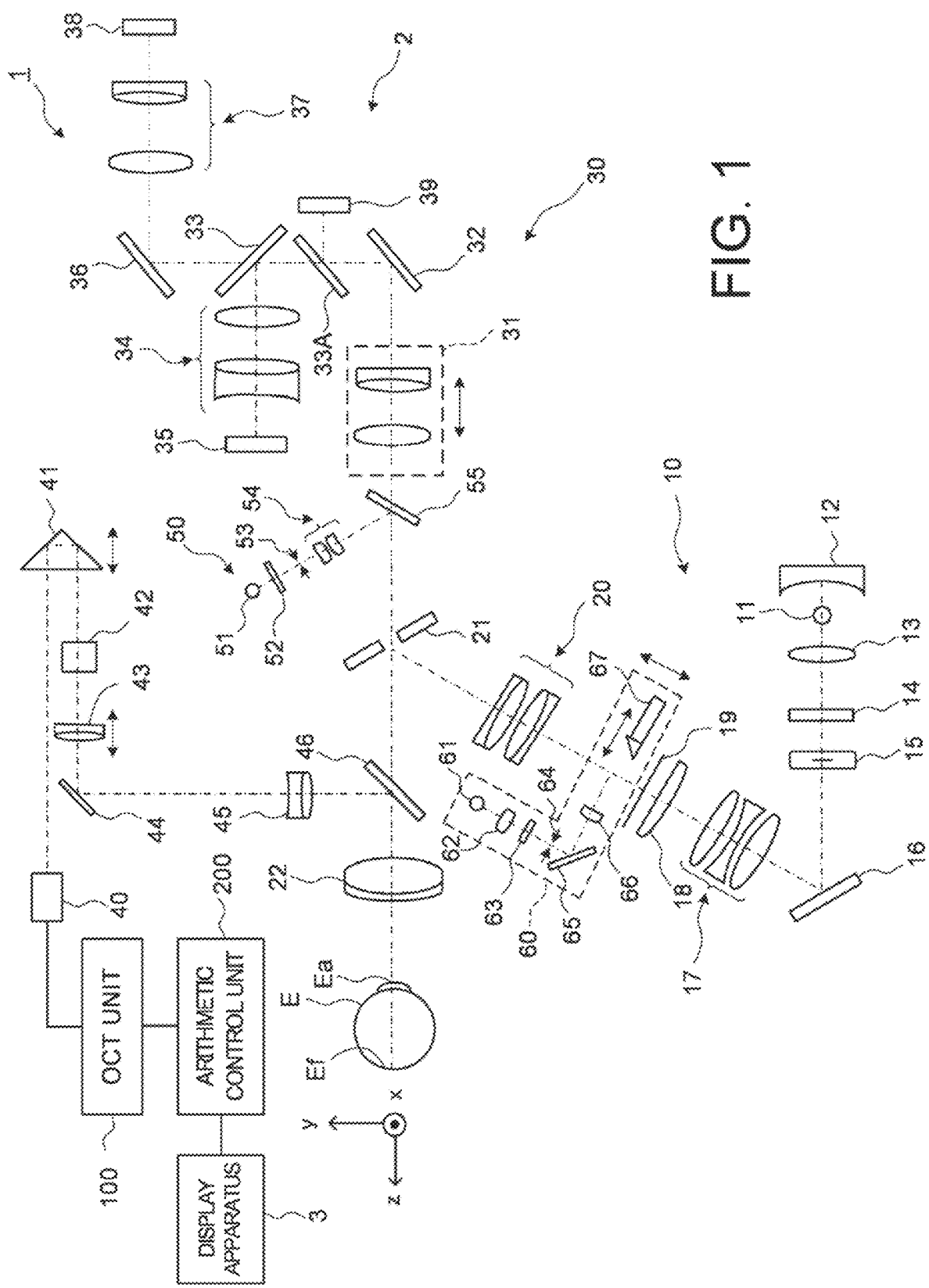
FIG. 1 is a schematic diagram illustrating an example of a configuration of an ophthalmologic apparatus according to embodiments.

In recent years, it is desired to easily obtain measurement results in a wider range using OCT measurement. Conventionally, in order to obtain OCT measurement results in a wide range, the measurement site is moved by changing the projected position of the fixation target on the fundus of the subject's eye. However, the process of repeating the OCT measurement while changing the projected position of the fixation target has a problem that the measurement time becomes long and a burden is placed on the examiner or the subject.

On the other hand, hand, it is considered that a result of OCT measurement in a wider range can be obtained by performing wide-angle OCT measurement.

In the swept source OCT and the spectral domain OCT, the OCT measurement range in the depth direction is determined by the spectral resolution that can be detected by the apparatus ("Optical Coherence Tomography: Technology and Applications", W. Drexler and J. G. Fujimoto, Springer, Berlin, p. 83, equation 2.18), and the optical resolution in the depth direction is determined by the wavelength width of the spectrum (ibid., p. 71, equation 2.8).

The OCT measurement range in the depth direction in the swept source OCT is represented by Equation (1) ("High-speed OCT light sources and systems [Invited]" (T. Klein and R. Huber, Biomedical Optics Express, U.S.A., Jan. 13, 2017, Vol. 8, No. 2, pp. 823-859)). In Equation (1), $z_{max}$ represents the OCT measurement range in the depth direction, a represents a coefficient, $\lambda_c$ represents a center wavelength, $\Delta\lambda$ represents a wavelength sweep width, $f_s$ represents a sampling speed of A/D converter which performs sampling of detection result of the interference light, and $f_{sweep}$ represents a wavelength sweep speed.

[Equation 1]

$$z_{max} = \alpha \times \frac{\lambda_c^2}{\Delta\lambda} \times \frac{f_s}{4 f_{sweep}} \quad (1)$$

In swept source OCT, by increasing the wavelength sweep speed, OCT measurement can be speeded up. Further, as shown in Equation (1), by changing the wavelength sweep speed, the OCT measurement range can be changed. However, the sampling speed of the A/D converter is limited. Thereby, there is a trade-off relationship between the speed-up of OCT measurement and the OCT measurement range in the depth direction.

Further, "Ultra-widefield retinal MHz-OCT imaging with up to 100 degrees viewing angle" (J. P. Kolb et al., Biomedical Optics Express, U.S.A., Apr. 2, 2015, Vol. 6, No. 5, pp. 1534-1552) discloses that a difference of optical path lengths occurs due to a displacement between a deflection center position of the measurement light, which is arranged in a pupil region during fundus scanning, and a curvature center position of the shape of the fundus. Therefore, in case of performing wide-angle OCT measurement, due to the difference of the optical path lengths caused by the displacement, a wider measurement range in the depth direction is required.

As described above, in swept source OCT, although wide-angle OCT measurement requires a wider measurement range in the depth direction, widening the measurement range limits the increase in the wavelength sweep speed.

In spectral domain OCT, the number of pixels of the CCD image sensor for obtaining the spectrum data is limited. Thereby, there is a trade-off relationship between the optical resolution in the depth direction and the OCT measurement range in the depth direction. Further, in spectral domain OCT, it is known that since the coherence length is determined by the resolution of spectroscopic measurement, the sensitivity decrease in the depth direction becomes great compared to the swept source OCT in which the coherence length is determined by the spectral line width of the wavelength sweep light source ("Optical Coherence Tomography: Technology and Applications" described above, p. 324). This also limits the OCT measurement range in the depth direction.

As described above, in spectral domain OCT, it is considered difficult to widen the measurement range in principle.

According to some embodiments of the present invention, a new technique for easily performing high-speed and wide-angle OCT measurement can be provided.

Referring now to the drawings, exemplary embodiments of an ophthalmologic apparatus and a method of controlling the ophthalmologic apparatus according to the present invention are described below. Any of the contents of the documents cited in the present specification and arbitrary known techniques may be applied to the embodiments below.

An ophthalmologic apparatus according to embodiments can form a tomographic image, a front image, and a three-dimensional image of a subject's eye by performing OCT based on measurement light generated using light from a light source. Examples of OCT includes Fourier domain OCT and time domain OCT. Examples of the Fourier domain OCT includes swept source OCT and spectral domain OCT. The ophthalmologic apparatus acquires a result of high-speed and wide-angle OCT measurement by performing a plurality of high-speed OCT measurements while changing scan region using an optical scanner deflecting the measurement light in a state where a projected position of fixation light flux on a fundus of the subject's eye is fixed. In some embodiments, by changing a reference position of a measurement range in a depth direction in accordance with a position of a scan region, a result of wide-angle OCT measurement corresponding to a shape of the fundus of the subject's eye can be acquired. In some embodiments, by changing a measurement range in a depth direction in accordance with a position of a scan region, a result of wide-angle OCT measurement corresponding to the shape of the fundus of the subject's eye can be acquired.

In the following embodiments, a configuration to which Fourier domain OCT (in particular, swept source OCT) is applied will be described. It should be noted that the configuration according to the embodiments can be applied to ophthalmologic apparatuses using other types of OCT than Fourier domain OCT (swept source OCT). In this specification, an image acquired using OCT may be collectively referred to as an "OCT image". Also, the measurement operation for forming OCT images may be referred to as OCT measurement.

The ophthalmologic apparatus according to some embodiments includes any one or more of an ophthalmologic imaging apparatus, an ophthalmologic measuring apparatus, and an ophthalmologic therapy apparatus. The ophthalmologic imaging apparatus included in the ophthalmologic apparatus according to some embodiments includes any one or more of a fundus camera, a scanning laser ophthalmoscope, a slit lamp microscope, a surgical microscope, and the like, for example. Further, the ophthalmologic measuring apparatus included in the ophthalmologic apparatus according to some embodiments includes any one or more of an eye refractivity examination apparatus, a tonometer, a specular microscope, a wave-front analyzer, a perimeter, a microperimeter, and the like, for example. Further, the ophthalmologic therapy apparatus included in the ophthalmologic apparatus according to some embodiments includes any one or more of a laser therapy apparatus, a surgical apparatus, a surgical microscope, and the like, for example.

The ophthalmologic apparatus according to the following embodiments includes an OCT apparatus and a fundus camera. The OCT apparatus can perform OCT measurement. Alternatively, the configuration according to the following embodiments may be applied to a single-functional OCT apparatus.

Hereinafter, an ophthalmologic apparatus capable of performing OCT measurement on a fundus of the subject's eye will be described as an example. However, the ophthalmologic apparatus according to the embodiments may be capable of performing OCT measurement on an anterior segment of the subject's eye. In some embodiments, a measurement site of the OCT measurement and/or a range of the OCT measurement are changed by moving a lens for changing focal position of the measurement light. In some embodiments, the ophthalmologic apparatus has a configuration capable of performing OCT measurement on the fundus, OCT measurement on the anterior segment, and OCT measurement on the whole eyeball including the fundus and anterior segment, by adding one or more attachments (objective lens, front lens, etc.). In some embodiments, in the ophthalmologic apparatus for measuring fundus, OCT measurement is performed on the anterior segment, by making the measurement light incident on the subject's eye, the measurement light having been converted into a parallel light flux by arranging a front lens between the objective lens and the subject's eye.

<Configuration>
[Optical System]

As shown in FIG. 1, the ophthalmologic apparatus 1 includes a fundus camera unit 2, an OCT unit 100, and an arithmetic control unit 200. The fundus camera unit 2 is provided with an optical system and a mechanism for acquiring front images of a subject's eye E. The OCT unit 100 is provided with a part of an optical system and a mechanism for performing OCT. Another part of the optical system and the mechanism for performing OCT are provided in the fundus camera unit 2. The arithmetic control unit 200 includes one or more processors for performing various kinds of arithmetic processing and control processing. In addition to these elements, an arbitrary element or a unit, such as a member (chin rest, forehead pad, etc.) for supporting a face of the subject, a lens unit (for example, an attachment for an anterior segment OCT) for switching the target site of OCT, and the like, may be provided in the ophthalmologic apparatus 1. In some embodiments, the lens unit is configured to be manually inserted and removed between the subject's eye E and an objective lens 22 described later. In some embodiments, the lens unit is configured to be automatically inserted and removed between the subject's eye E and the objective lens 22 described later, under the control of the controller 210 described later.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

[Fundus Camera Unit]

The fundus camera unit 2 is provided with an optical system for imaging (photographing) a fundus Ef of the subject's eye E. An image (called fundus image, fundus photograph, etc.) of the fundus Ef to be obtained is a front image such as an observation image, a photographic image, or the like. The observation image is obtained by moving image shooting using near infrared light. The photographic image is a still image using flash light. Furthermore, the fundus camera unit 2 can obtain the front image (anterior segment image) by photographing (imaging) an anterior segment Ea of the subject's eye E.

The fundus camera unit 2 includes an illumination optical system 10 and an imaging (photographing) optical system 30. The illumination optical system 10 projects illumination light onto the subject's eye E. The imaging optical system 30 detects returning light of the illumination light from the subject's eye E. Measurement light from the OCT unit 100 is guided to the subject's eye E through an optical path in the fundus camera unit 2. Returning light of the measurement light is guided to the OCT unit 100 through the same optical path.

Light (observation illumination light) emitted from the observation light source 11 of the illumination optical system 10 is reflected by a reflective mirror 12 having a curved reflective surface, and becomes near-infrared light after penetrating a visible cut filter 14 via a condenser lens 13. Further, the observation illumination light is once converged near an imaging light source 15, is reflected by a mirror 16, and passes through relay lenses 17 and 18, a diaphragm 19, and a relay lens 20. Then, the observation illumination light is reflected on the peripheral part (the surrounding area of a hole part) of a perforated mirror 21, penetrates a dichroic mirror 46, and is refracted by an objective lens 22, thereby illuminating the subject's eye E (fundus Ef or anterior segment Ea). Returning light of the observation illumination light reflected from the subject's eye E is refracted by the objective lens 22, penetrates the dichroic mirror 46, passes through the hole part formed in the center area of the perforated mirror 21, penetrates a dichroic mirror 55. The returning light penetrating the dichroic mirror 55 travels through a photography focusing lens 31 and is reflected by a mirror 32. Further, this returning light penetrates a half mirror 33A, is reflected by a dichroic mirror 33, and forms an image on the light receiving surface of an image sensor 35 by a condenser lens 34. The image sensor 35 detects the returning light at a predetermined frame rate. It should be noted that the focus of the imaging optical system 30 is adjusted so as to coincide with the fundus Ef or the anterior segment Ea.

Light (imaging illumination light) emitted from the imaging light source 15 is projected onto the fundus Ef via the same route as that of the observation illumination light. Returning light of the imaging illumination light from the subject's eye E is guided to the dichroic mirror 33 via the same route as that of the observation illumination light, penetrates the dichroic mirror 33, is reflected by a mirror 36, and forms an image on the light receiving surface of the image sensor 38 by a condenser lens 37.

A liquid crystal display (LCD) 39 displays a fixation target and a visual target used for visual acuity measurement. Part of light output from the LCD 39 is reflected by the half mirror 33A, is reflected by the mirror 32, travels through the photography focusing lens 31 and the dichroic mirror 55, and passes through the hole part of the perforated mirror 21. The light flux (beam) having passed through the hole part of the perforated mirror 21 penetrates the dichroic mirror 46, and is refracted by the objective lens 22, thereby being projected onto the fundus Ef.

By changing the display position of the fixation target on the screen of the LCD 39, the fixation position of the subject's eye E can be changed. Examples of the fixation position include a fixation position for acquiring an image centered at a macula, a fixation position for acquiring an image centered at an optic disc, a fixation position for acquiring an image centered at a fundus center between the macula and the optic disc, a fixation position for acquiring an image of a site (fundus peripheral part) far away from the macula, and the like. The ophthalmologic apparatus 1 according to some embodiments includes GUI (Graphical User Interface) and the like for designating at least one of such fixation positions. The ophthalmologic apparatus 1 according to some embodiments includes GUI etc. for manually moving the fixation position (display position of the fixation target).

The configuration for presenting the movable fixation target to the subject's eye E is not limited to the display device such LCD or the like. For example, the movable fixation target can be generated by selectively turning on a plurality of light sources of a light source array (light emitting diode (LED) array or the like). Alternatively, the movable fixation target can be generated using one or more movable light sources.

Further, the ophthalmologic apparatus 1 may be provided with one or more external fixation light sources. One of the one or more external fixation light sources can project fixation light onto a fellow eye of the subject's eye E. A projected position of the fixation light on the fellow eye can be changed. By changing the projected position of the fixation light on the fellow eye, the fixation position of the subject's eye E can be changed. The projected position by the external fixation light source(s) may be the same as the projected position of the subject's eye E using the LCD 39. For example, the movable fixation target can be generated by selectively turning on a plurality of external fixation light sources. Alternatively, the movable fixation target can be generated using one or more movable external fixation light sources.

The alignment optical system 50 generates an alignment indicator for alignment of the optical system with respect to the subject's eye E. Alignment light emitted from an LED 51 travels through the diaphragms 52 and 53 and the relay lens 54, is reflected by the dichroic mirror 55, and passes through the hole part of the perforated mirror 21. The alignment light having passed through the hole part of the perforated mirror 21 penetrates the dichroic mirror 46, and is projected onto the subject's eye E by the objective lens 22. Corneal reflection light of the alignment light is guided to the image sensor 35 through the same route as the returning light of the observation illumination light. Manual alignment or automatic alignment can be performed based on the received light image (alignment indicator image) thereof.

The focus optical system 60 generates a split indicator for adjusting the focus with respect to the subject's eye E. The focus optical system 60 is movable along an optical path (illumination optical path) of the illumination optical system 10 in conjunction with the movement of the photography focusing lens 31 along an optical path (imaging optical path) of the imaging optical system 30. The reflection rod 67 can be inserted and removed into and from the illumination optical path. To conduct focus adjustment, the reflective surface of the reflection rod 67 is arranged in a slanted position on the illumination optical path. Focus light emitted from an LED 61 passes through a relay lens 62, is split into two light beams by a split indicator plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the perforated mirror 21, penetrates the dichroic mirror 46, and is refracted by the objective lens 22, thereby being projected onto the fundus Ef. Fundus reflection light of the focus light is guided to the image sensor 35 through the same route as the corneal reflection light of the alignment light. Manual focus or automatic focus can be performed based on the received light image (split indicator image) thereof The dichroic mirror 46 combines an optical path for fundus photography and an optical path for OCT. The dichroic mirror 46 reflects light of wavelength band used in OCT, and transmits light for fundus photography. The optical path for OCT (optical path of measurement light) is provided with, in order from the OCT unit 100 side to the dichroic mirror 46 side, a collimator lens unit 40, an optical path length changing unit 41, an optical scanner 42, an OCT focusing lens 43, a mirror 44, and a relay lens 45.

The optical path length changing unit 41 is movable in directions indicated by the arrow in FIG. 1, thereby changing the length of the optical path for OCT. This change in the optical path length is used for correcting the optical path length according to the axial length, adjusting the interference state, or the like. The optical path length changing unit 41 includes a corner cube and a mechanism for moving the corner cube.

The optical scanner 42 is disposed at a position optically conjugate with the pupil of the subject's eye E. The optical scanner 42 deflects the measurement light LS traveling along the OCT optical path. The optical scanner 42 is a galvano scanner capable of scanning two-dimensionally, for example.

The OCT focusing lens 43 is moved along the optical path of the measurement light LS in order to perform focus adjustment of the optical system for OCT. The OCT focusing lens 43 can move within a moving range. The moving range includes a first lens position for placing the focal position of the measurement light LS at the fundus Ef or near the fundus Ef of the subject's eye E and a second lens position for making the measurement light LS projected onto the subject's eye E a parallel light beam. The movement of the photography focusing lens 31, the movement of the focus optical system 60, and the movement of the OCT focusing lens 43 can be controlled in conjunction with each other.

[Oct Unit]

Figure 2:
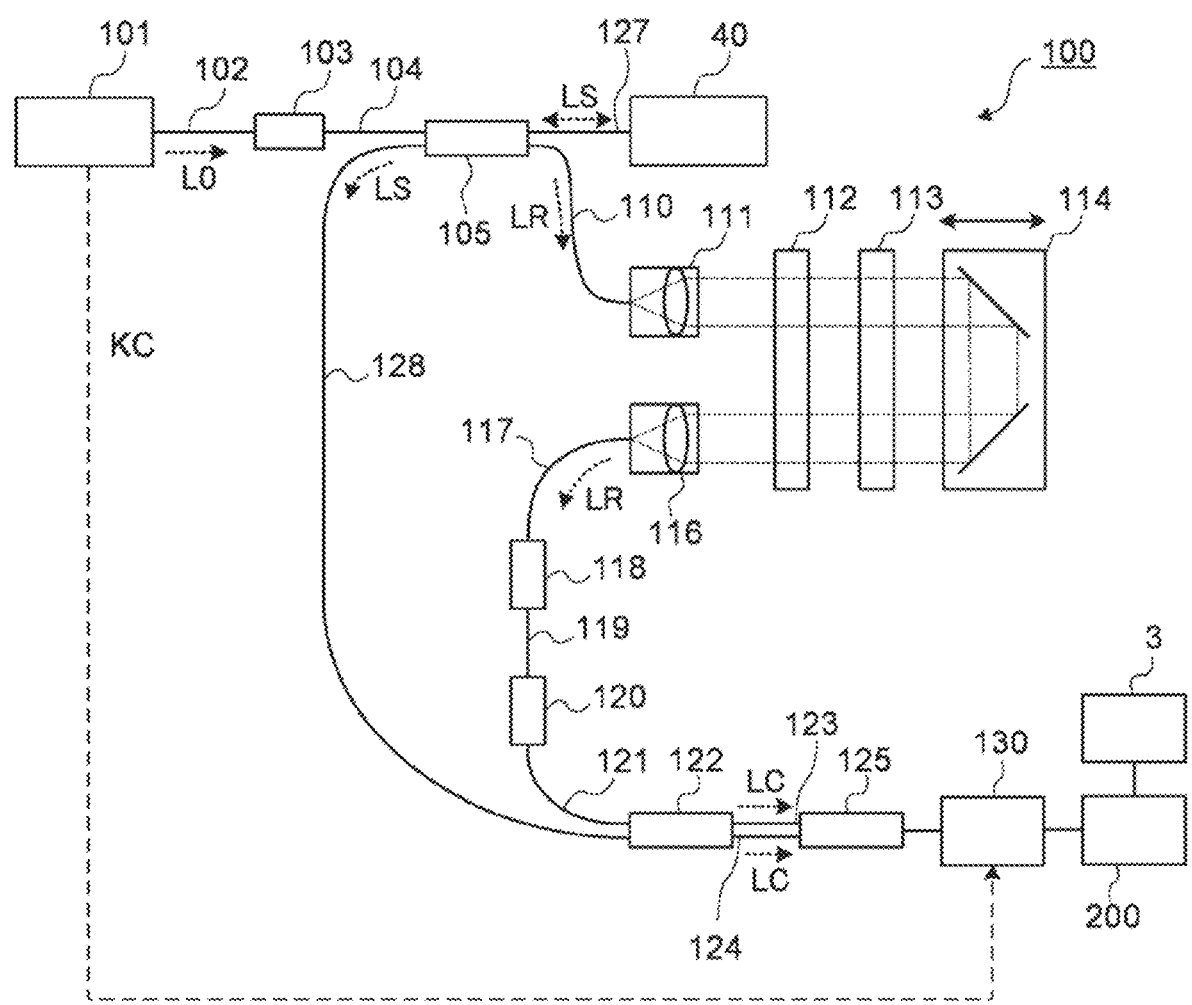
FIG. 2 is a schematic diagram illustrating an example of a configuration of the ophthalmologic apparatus according to the embodiments.
Figure 3:
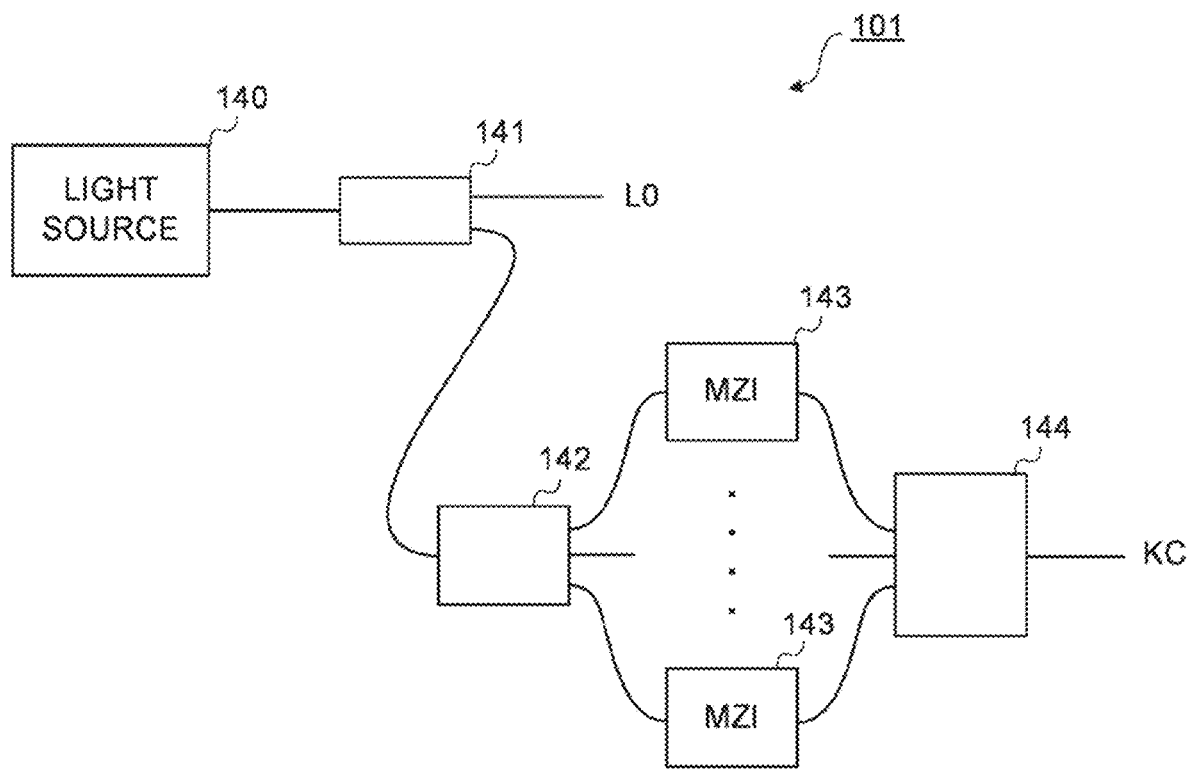
FIG. 3 is a schematic diagram illustrating an example of a configuration of the ophthalmologic apparatus according to the embodiments.

As illustrated by an example in FIGS. 2 and 3, the OCT unit 100 is provided with an optical system for performing swept source OCT. This optical system includes an interference optical system. This interference optical system has a function that splits light from the wavelength sweep type (wavelength tunable type) light source into measurement light and reference light, a function that makes the returning light of the measurement light from the subject's eye E and the reference light having traveled through a reference optical path interfere with each other and generates interference light, and a function that detects the interference light. The detection result (detection signal) of the interference light obtained by the interference optical system is a signal indicating a spectrum of the interference light, and is sent to the arithmetic control unit 200.

As illustrated by an example in FIG. 3, the light source unit 101 emits light L0 and a clock KC. The light L0 is wavelength sweep light obtained by sweeping in a predetermined wavelength range at a changeable wavelength sweep speed. The clock KC is generated from the wavelength sweep light. Such a light source unit 101 includes a light source 140, optical splitters 141 and 142, a plurality of Mach-Zehnder interferometers (MZI) 143, and an optical selection output device 144. The optical elements within the light source unit 101 are optically connected to each other via optical fibers.

The light source 140 is a wavelength sweep light source which emits the wavelength sweep light in which the center wavelength of emitted light changes at high speed by sweeping a predetermined wavelength range at a changeable wavelength sweep speed. The light source 140 includes a near-infrared tunable laser, for example.

The optical splitter 141 splits the wavelength sweep light emitted from the light source 140 into the light L0 and light for clock generation. The light L0 split by the optical splitter 141 is guided to a polarization controller 103 through an optical fiber 102. The light for clock generation split by the optical splitter 141 is guided to the optical splitter 142 through an optical fiber. The optical splitter 142 splits the light for clock generation into a plurality of split light (for example, split light for the number of measurement modes). Each of the plurality of split light which is split by the optical splitter 142 is guided to any one of a plurality of MZIs 143 through an optical fiber.

The MZI 143 further splits the split light, which is split by the optical splitter 142, into two light, and outputs composed light corresponding to a difference between the optical path lengths of the optical paths by composing two optical paths passing through different optical paths. The plurality of MZIs 143 is configured so that the differences of the optical path lengths are different from each other in accordance with the wavelength sweep speeds which are changed according to the measurement range. The optical selection output device 144 selectively outputs, as the clock KC, the composed light from the plurality of the MZIs 143 based on the wavelength sweep speed changed in accordance with the measurement range.

In some embodiments, the plurality of the MZIs 143 is provided by the number of measurement modes having different measurement ranges. In some embodiments, the plurality of the MZIs 143 is provided for the number of scan regions different scan region to perform wide-angle OCT measurement.

The plurality of the MZIs 143 can be configured to have differences of the optical path lengths, which are different from each other, according to the measurement modes having different measurement ranges, and the optical selection output device 144 can be configured to selectively output the composed light according to the wavelength sweep speed. Thereby, the composed light in which the change in the wavelength sweep speed is canceled can be output. Thus, the clock KC output from the optical selection output device 144 is output a clock having a constant frequency (cycle). It should be noted that the number of MZIs 143 is arbitrary as long as the clock KC can be output as a clock having a constant frequency.

As shown in FIG. 2, the light L0 emitted from the light source unit 101 is guided to the polarization controller 103 through the optical fiber 102, and the polarization state of the light L0 is adjusted. The light L0 whose polarization state has been adjusted is guided to the fiber coupler 105 through the optical fiber 104. The fiber coupler 105 splits the light L0 into the measurement light LS and the reference light LR.

The reference light LR is guided to the collimator 111 through the optical fiber 110. The reference light LR is converted into a parallel light beam by the collimator 111. Then, the reference light LR is guided to the corner cube 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS. The corner cube 114 is movable in the incident direction of the reference light LR. With this, the length of the optical path of the reference light LR is changed.

The reference light LR that has traveled through the corner cube 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through an optical fiber 127, and is made into a parallel light beam by the collimator lens unit 40. The measurement light LS made into the parallel light beam travels through the optical path length changing unit 41, the optical scanner 42, the OCT focusing lens 43, the mirror 44, and the relay lens 45. The measurement light LS having traveled through the relay lens 45 is reflected by the dichroic mirror 46, is refracted by the objective lens 22, and is irradiated onto the subject's eye E. The measurement light LS is scattered and reflected at various depth positions of the subject's eye E. Returning light of the measurement light LS from the subject's eye E advances in the same path as the forward path in the opposite direction, is guided to the fiber coupler 105, and then reaches the fiber coupler 122 via the optical fiber 128.

The fiber coupler 122 combines (interferes) the measurement light LS incident through the optical fiber 128 and the reference light LR incident through the optical fiber 121 to generate interference light. The fiber coupler 122 splits the interference light at a predetermined splitting ratio (e.g., 1:1) to generate a pair of interference light LC. The pair of interference light LC is guided to a detector 125 through optical fibers 123 and 124, respectively.

The detector 125 is a balanced photodiode, for example. The balanced photodiode includes a pair of photodetectors in which each photodiode detects each of the pair of interference light LC. The balanced photodiode outputs the difference between a pair of detection results acquired by the pair of photodetectors. The detector 125 sends the output (detection signal) to a DAQ (data acquisition system) 130.

A clock KC is supplied from the light source unit 101 to the DAQ 130. The clock KC is a clock having a substantially constant frequency even when the wavelength sweep speed is changed in the light source unit 101, as described above. The DAQ 130 performs A/D conversion on the detection signal input from the detector 125 in synchronization with the clock KC, and samples the result of the A/D conversion as an interference signal. The DAQ 130 sends the interference signal obtained by sampling to the arithmetic control unit 200.

In the present examples, both the optical path length changing unit 41 that changes the length of the optical path of the measurement light LS (i.e., measurement optical path or measurement arm) and the corner cube 114 that changes the length of the optical path of the reference light LR (i.e., reference optical path or reference arm) are provided. Alternatively, any one of the optical path length changing unit 41 and the corner cube 114 may be provided. The difference between the measurement optical path length and the reference optical path length can be changed using other optical members.

[Arithmetic Control Unit]

The arithmetic control unit 200 analyzes the detection signals fed from the DAQ 130 to form an OCT image of the fundus Ef. The arithmetic processing for the OCT image formation is performed in the same manner as in the conventional swept-source-type OCT apparatus.

In addition, the arithmetic control unit 200 controls each part of the fundus camera unit 2, the display apparatus 3, and the OCT unit 100.

As the control for the fundus camera unit 2, the arithmetic control unit 200 performs following controls: the operation control of the observation light source 11, of the imaging light source 15 and of the LEDs 51 and 61; the operation control of the LCD 39; the movement control of the photography focusing lens 31; the movement control of the OCT focusing lens 43; the movement control of the reflection rod 67; the movement control of the focus optical system 60; the movement control of the optical path length changing unit 41; the operation control of the optical scanner 42, and the like.

As the control of the OCT unit 100, the arithmetic control unit 200 performs following controls: the operation of the light source unit 101; the operation of the polarization controllers 103 and 118, the operation of the attenuator 120; the operation of the detector 125; the operation of the DAQ 130; and the like.

As in the conventional computer, the arithmetic control unit 200 includes a microprocessor, RAM, ROM, hard disk drive, and communication interface, for example. A storage device such as the hard disk drive stores a computer program for controlling the ophthalmologic apparatus 1. The arithmetic control unit 200 may include various kinds of circuitry such as a circuit board for forming OCT images. In addition, the arithmetic control unit 200 may include an operation device (or an input device) such as a keyboard and a mouse, and a display device such as an LCD.

The fundus camera unit 2, the display apparatus 3, the OCT unit 100, and the arithmetic control unit 200 may be integrally provided (i.e., in a single housing), or they may be separately provided in two or more housings.

[Control System]

Figure 4:
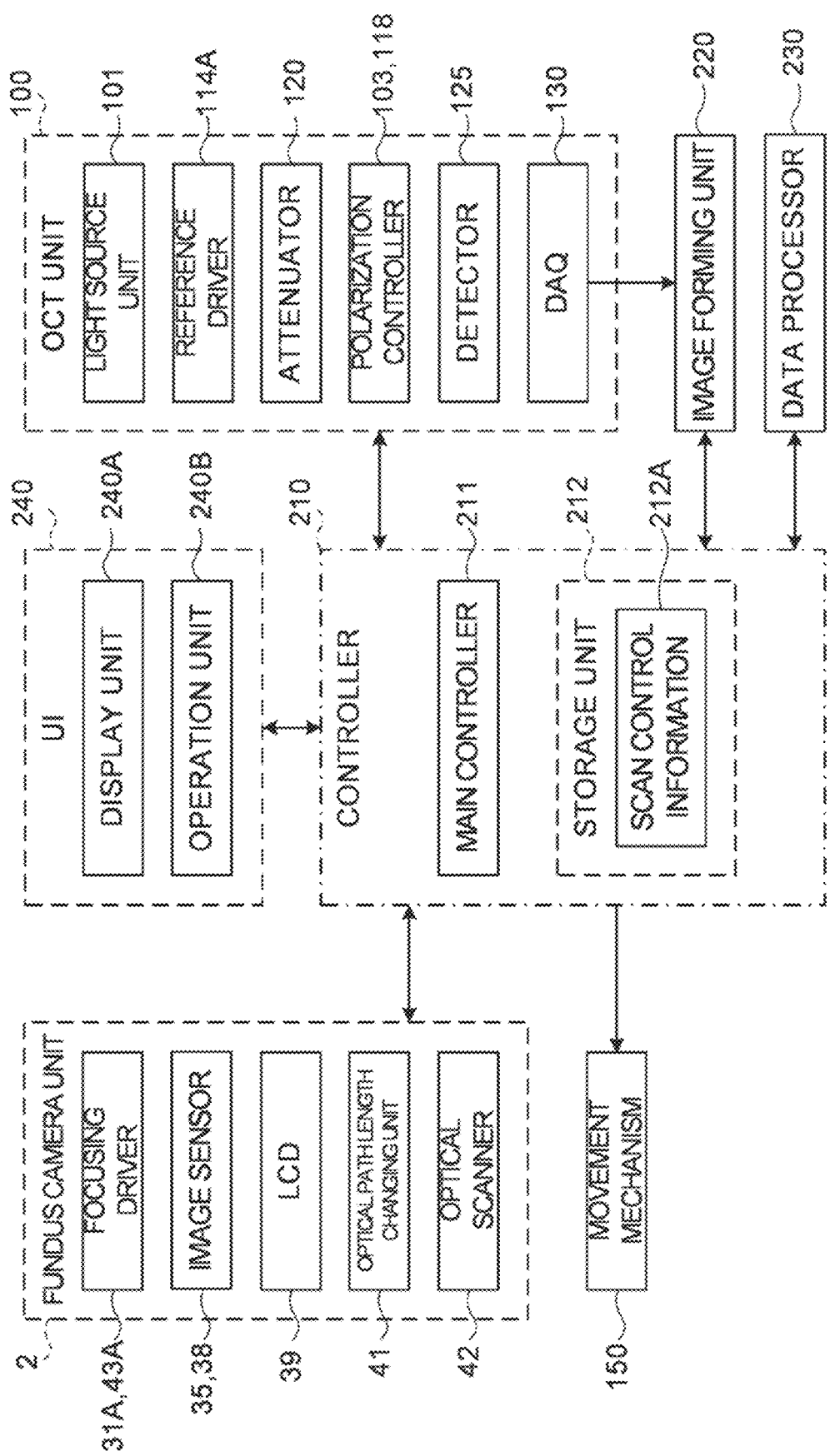
FIG. 4 is a schematic block diagram illustrating an example of the configuration of the ophthalmologic apparatus according to the embodiments.
Figure 5:
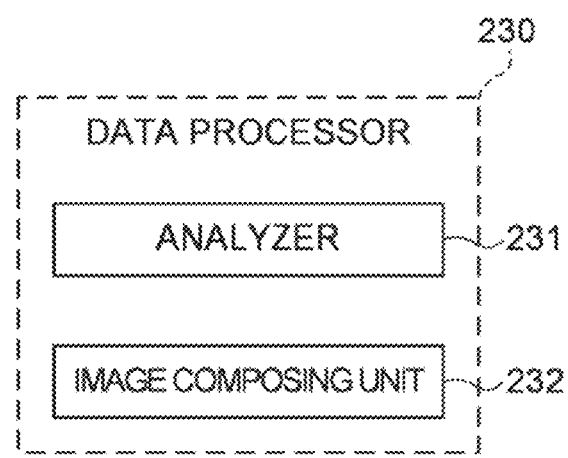
FIG. 5 is a schematic block diagram illustrating an example of the configuration of the ophthalmologic apparatus according to the embodiments.

FIGS. 4 and 5 illustrate a configuration example of a control system of the ophthalmologic apparatus 1. In FIGS. 4 and 5, a part of the components included in the ophthalmologic apparatus 1 is omitted. FIG. 5 shows a block diagram of an example of the configuration of the data processor 230 of FIG. 4. For example, the arithmetic control unit 200 is provided with a controller 210, an image forming unit 220, and a data processor 230.

(Controller)

The controller 210 executes various controls. The controller 210 includes a main controller 211 and a storage unit 212.

(Main Controller)

The main controller 211 includes a processor and controls each part of the ophthalmologic apparatus 1. For example, the main controller 211 controls the components of the fundus camera unit 2, such as the optical path length changing unit 41, the optical scanner 42, the photography focusing lens 31 (focusing driver 31A), and the focus optical system 60, the OCT focusing lens 43 (focusing driver 43A), the image sensors 35 and 38, the LCD 39, and the entire optical system (movement mechanism 150), and the like. Further, the main controller 211 controls components of the OCT unit 100 such as the light source unit 101, the corner cube 114 (reference driver 114A), the attenuator 120, the polarization controllers 103 and 118, the detector 125, and the DAQ 130.

For example, the main controller 211 controls the LCD 39 to display the fixation target at a position on the screen of the LCD 39 corresponding the fixation position set manually or automatically. Moreover, the main controller 211 can change the display position of the fixation target displayed on the LCD 39 (in a continuous manner or in a phased manner). Thereby, the fixation target can be moved (that is, the fixation position can be changed). The display position of the fixation target and movement mode of the fixation target are set manually or automatically. Manual setting is performed using GUI, for example. Automatic setting is performed by the data processor 230, for example.

The focusing driver 31A moves the photography focusing lens 31 in the direction along the optical axis of the imaging optical system 30, and moves the focus optical system 60 in the direction along the optical axis of the illumination optical system 10. With this, the focal position of the imaging optical system 30 is changed. The focusing driver 31A may include a dedicated mechanism for moving the photography focusing lens 31 and a dedicated mechanism for moving the focus optical system 60. The focusing driver 31A is controlled when performing focus adjustment or the like.

The focusing driver 43A moves the OCT focusing lens 43 in the optical axis direction of the measurement optical path. As a result, the focus position of the measurement light LS is changed. For example, the focus position of the measurement light LS can be arranged at the fundus Ef or near the fundus Ef by moving the OCT focusing lens 43 to the first lens position. For example, the focus position of the measurement light LS can be arranged at a far point position by moving the OCT focusing lens 43 to the second lens position. The focus position of the measurement light LS corresponds to the depth position (z position) of the beam waist of the measurement light LS.

The movement mechanism 150 three-dimensionally moves at least the fundus camera unit 2 (optical system), for example. In a typical example, the movement mechanism 150 includes a mechanism for moving at least the fundus camera unit 2 in the x direction (left-right direction, horizontal direction), a mechanism for moving it in the y direction (up-down direction, vertical direction), and a mechanism for moving it in the z direction (depth direction, front-back direction). The mechanism for moving in the x direction includes a x stage movable in the x direction and a x movement mechanism for moving the x stage, for example. The mechanism for moving in the y direction includes a y stage movable in the y direction and a y movement mechanism for moving the y stage, for example. The mechanism for moving in the z direction includes a z stage movable in the z direction and a z movement mechanism for moving the z stage, for example. Each movement mechanism includes an actuator such as a pulse motor, and operates under the control of the main controller 211.

The control for the movement mechanism 150 is used for alignment and tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement. In some embodiments, the movement mechanism 150 is configured to be controlled to change the optical path length of the reference light (that is, the difference of the optical path length between the optical path of the measurement light and the optical path of the reference light).

In the case of manual alignment, a user operates a user interface (UI) 240 described later to relatively move the optical system and subject's eye E so as to cancel the displacement of the subject's eye E with respect to the optical system. For example, the main controller 211 controls the movement mechanism 150 to relatively move the optical system and the subject's eye E by outputting a control signal corresponding to the operation content with respect to the user interface 240 to the movement mechanism 150.

In the case of automatic alignment, the main controller 211 controls the movement mechanism 150 to relatively move the optical system and the subject's eye E so as to cancel the displacement of the subject's eye E with respect to the optical system. In some embodiments, the main controller 211 controls the movement mechanism 150 to relatively move the optical system and the subject's eye E by outputting a control signal to the movement mechanism 150 so that the optical axis of the optical system substantially coincides with the axis of the subject's eye E and the distance of the optical system with respect to the subject's eye E is a predetermined working distance. Here, the working distance is a preset value which is called a working distance of the objective lens 22, and it means the distance between the subject's eye E and the optical system when measuring (imaging) using the optical system.

The main controller 211 sequentially performs a plurality of OCT measurements on a plurality of scan regions different from each other, by controlling the OCT unit 100 and the optical scanner 42 in a state where a display position of the fixation target on the LCD 39 is fixed. In some embodiments, at least two scan regions are set so as to be overlapped. Thereby, a plurality of measurement results obtained by performing OCT measurements on the plurality of scan regions can be easily composed.

Figure 6:
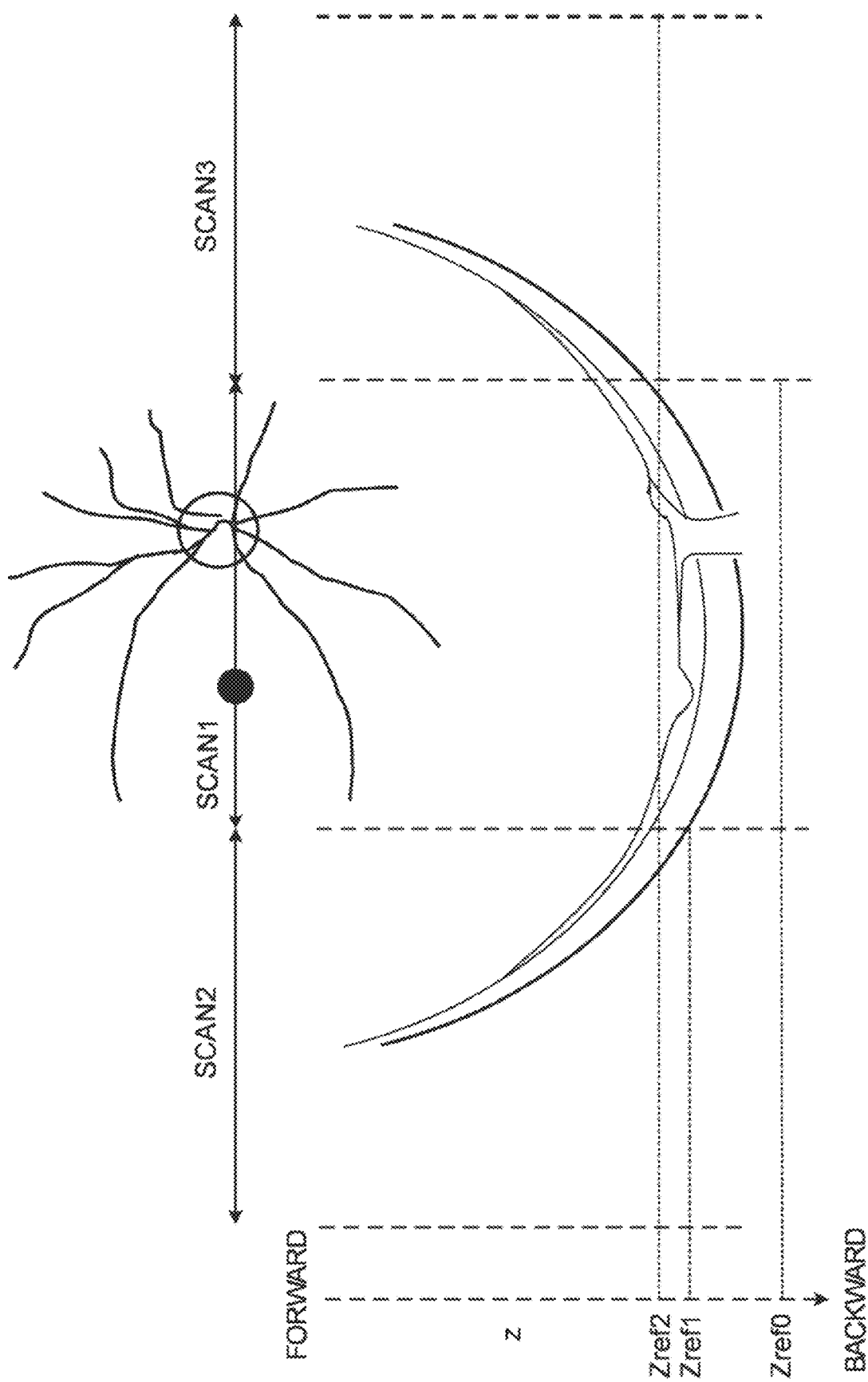
FIG. 6 is a schematic diagram for explaining processing performed by the ophthalmologic apparatus according to the embodiments.

FIG. 6 shows a diagram explaining the operation of the ophthalmologic apparatus 1 according to the embodiments. FIG. 6 schematically represents a fundus image and a tomographic image of the fundus Ef of the subject's eye E.

The main controller 211 controls to performing OCT measurement on the first scan region SCAN1. In some embodiments, the first scan region SCAN1 includes at least one of a region corresponding to a optic disc and a region corresponding to a fovea. In some embodiments, a scan center position of the first scan region SCAN1 is a position of an optical axis of the optical system on the fundus Ef after performing alignment. In some embodiments, a reference position Zref0 of the measurement range in the depth direction of the scan on the first scan region SCAN1 is a depth position where the optical path length of the measurement light and the optical path length of the reference light match.

Subsequently, the main controller 211 controls to perform OCT measurement on the second scan region SCAN2 in a state where the fixation target is displayed on the LCD 39 at the same display position as when scanning for the first scan region SCAN1. The scan center position of the second scan region SCAN2 is a position separated by a predetermined distance d1 from the scan center position of the first scan region SCAN1. The main controller 211 can change the difference of the optical path lengths between the optical path of the measurement light LS and the optical path of the reference light LR by controlling the optical path length changing unit 41 (or the corner cube 114 and the reference driver 114A) in accordance with a position of the scan region, and can change the reference position of the measurement range in the depth direction of the OCT measurement. In FIG. 6, the reference position Zref1 of the measurement range in the depth direction is changed. In some embodiments, the main controller 211 changes the wavelength sweep speed by controlling the light source 140, and changes the measurement range in the depth direction of the OCT measurement. In some embodiments, the main controller 211 changes the reference position of the measurement range as described above while changing the measurement range in the depth direction of the OCT measurement.

Subsequently, the main controller 211 controls to perform OCT measurement on the third scan region SCAN3 in a state where the fixation target is displayed on the LCD 39 at the same display position as when scanning for the first scan region SCAN1. The scan center position of the third scan region SCAN3 is a position separated by a predetermined distance d2 from the scan center position of the first scan region SCAN1. The distance d2 may be the same as the distance d1. The main controller 211 changes the reference position of the measurement range in the depth direction for the third scan region SCAN3 to the reference position Zref2. In some embodiments, the main controller 211 changes the wavelength sweep speed by controlling the light source 140, and changes the measurement range in the depth direction of the OCT measurement. In some embodiments, the main controller 211 changes the reference position of the measurement range as described above while changing the measurement range in the depth direction of the OCT measurement.

Considering the shape of the fundus Ef, when the displacement amount of the scan center position of the scan region exceeds a predetermined distance, an OCT measurement range wider than the OCT measurement range shown in Expression (1) is required.

Therefore, the main controller 211 changes the difference of the optical path lengths described above, when a distance in a scan direction (for example, B scan direction of the first scan region SCAN1) between the scan center position of the first scan region SCAN1 and the scan center position of the second scan region SCAN2 (third scan region SCAN3)

exceeds a first distance. In some embodiments, the first distance is a distance of one side (for example, L described later) when the scan region is a rectangular region.

Here, it is assumed that each of the first scan region SCAN1 and the second scan region SCAN2 in the fundus Ef is L millimeters square. That is, it is assumed that a length in the B scan direction (scan length) is L millimeters. In this case, in case that OCT measurement, in which the measurement range in the depth direction is z0 millimeters and the scan length is L millimeters, is performed on each of the first scan region SCAN1 and the second scan region SCAN2, z0=0.4×L is approximately satisfied in the vicinity of the macula or the optic disc, in consideration of the shape of the fundus Ef. That is, in case that OCT measurement, in which the scan length L is 6 millimeters, is performed on the fundus Ef, the measurement range of approximately 2.4 millimeters in the depth direction is required.

Thus, in case that OCT measurement is performed on the second scan region SCAN2 in a region separated by a predetermined distance (for example, 6 millimeters) or more from the first scan region SCAN1 including a predetermined site in the fundus Ef of the subject's eye E, the main controller 211 changes the reference position of the measurement range in the depth direction by changing the difference of the optical path lengths described above when L is greater than (2.5×z0). Examples of the predetermined site in the fundus Ef include the macula and the optic disc. Thereby, the result of the OCT measurement can be acquired in a wide range in accordance with the shape of the fundus Ef.

In some embodiments, the main controller 211 changes the OCT measurement range by changing the wavelength sweep speed for each scan region. For example, the main controller 211 changes the OCT measurement range by performing change control of the wavelength sweep speed on the light source 140 in the light source unit 101.

In this case, when the measurement range in the depth direction required for OCT measurement is z0 millimeters, and the displacement of the scan center position in the B scan direction of the second scan region SCAN2 with respect to the scan center position of the first scan region SCAN1 is d, it is desirable to perform OCT measurement so as to satisfy Equation (2). With this, the scan region that can be performed at one time can be maximized. z0 is a range required for alignment in the z direction or for forming tomographic images.

[Equation 2]

$$z_{max} = \alpha \times \frac{\lambda_c^2}{\Delta\lambda} \times \frac{f_s}{4 f_{sweep}} \times 10^{-3} [\text{mm}] < z0 \ (0 < d \leq L) \quad (2)$$

In some embodiments, L is 12 millimeters and z0 is 2 millimeters.

Considering the difference of the optical path lengths caused by the displacement between the deflection center position of the measurement light arranged in the pupil region and the curvature center position of the fundus shape, in the range of d>L, it is desirable to perform OCT measurement so as to satisfy Equation (3). Thereby, the result of the OCT measurement can be acquired in a wide range in accordance with the shape of the fundus Ef.

[Equation 3]

$$z_{max} = \alpha \times \frac{\lambda_c^2}{\Delta\lambda} \times \frac{f_s}{4 f_{sweep}} \times 10^{-3} [\text{mm}] < z0 + 0.4 \times (d-L) \ (L < d) \quad (3)$$

In some embodiments, $\lambda_c$ is 1050 nanometers, $\Delta\lambda$ is 100 nanometers, and the coefficient $\alpha$ is 0.5 (wavelength sweep speed difference (maximum speed/minimum speed)), in Equations (2) and (3). In this case, Equation (3) can be expressed as $1.375\times10-3\times(f_s/f_{sweep})<z0+0.4\times(d-L)$.

As a method of increasing $z_{max}$ corresponding to the measurement range, as shown in Equation (1), there are (a) a method of increasing $f_s$ corresponding to the sampling speed of A/D conversion, (b) a method of reducing $\Delta\lambda$ corresponding to the wavelength sweep width, and (c) a method of reducing $f_{sweep}$, which is the wavelength sweep speed.

In the method (a), there is a limit in improving the sampling speed of the A/D converter. Therefore, it also has a limit in expanding the measurement range.

In the method (b), as shown in the following Equation (4) described in "High-speed OCT light sources and systems [Invited]" (T. Klein and R. Huber, Biomedical Optics Express, U.S.A., Jan. 13, 2017, Vol. 8, No. 2, pp. 823-859), reducing $\Delta\lambda$ causes a decrease in resolution in the depth direction. In Equation (4), $\Delta z$ represents a resolution in the depth direction, and $\Delta\lambda_{FWHM}$ represents a full width at half maximum of the wavelength.

[Equation 4]

$$\Delta z = \frac{2 \ln(2)}{\pi} \times \frac{\lambda_c^2}{\Delta\lambda_{FWHM}} \quad (4)$$

In the method (c), it becomes more susceptible to fixation disparity. As a result, the measurement accuracy is degraded and the image quality is degraded.

On the other hand, according to the embodiments, the wavelength sweep speed can be changed regardless of the sampling speed of the A/D converter. Thereby, the measurement range in the depth direction shown in Equation (1) can be changed without lowering the resolution in the depth direction shown in Equation (4).

The main controller 211 controls the fundus camera unit 2 etc. to control the fundus imaging (photography) and the anterior segment imaging. Further, the main controller 211 controls the fundus camera unit 2 and the OCT unit 100 etc. to control the OCT measurement. The main controller 211 is capable of performing a plurality of preliminary operations prior to OCT measurement. Examples of the preliminary operation include alignment, rough focus adjustment, polarization adjustment, and fine focus adjustment. The plurality of preliminary operations is performed in a predetermined order. In some embodiments, the plurality of preliminary operations is performed in an order described above.

It should be noted that the types and the orders of the preliminary operations are not so limited, and they may be optional. For example, the preliminary operations may further include small-pupil judgment. The small-pupil judgment is a preliminary operation to judge whether the pupil of the subject's eye E is small or not (whether the subject's eye E is microcoria or not). The small-pupil judgment may be performed between the rough focus adjustment and the optical path length difference adjustment. In some embodiments, the small-pupil judgment includes, for example, a series of processes as follows: acquiring a front image (anterior segment image) of the subject's eye E; specifying an image region corresponding to the pupil; calculating the size (e.g., diameter, circumference length) of the pupil region; judging whether the pupil of the subject's eye E is small or not based on the calculated size (threshold processing); and controlling the diaphragm 19 when judged that the pupil of the subject's eye E is small. In some embodiments, the calculation of the size of the pupil region includes processing of circularly or elliptically approximating the pupil region.

The rough focus adjustment is a kind of focus adjustment using the split indicator. The rough focus adjustment may be performed by determining the position of the photography focusing lens 31 based on information, which is obtained by associating the eye refractive power acquired in advance with the position of the photography focusing lens 31, and a measured value of the refractive power of the subject's eye E.

The fine focus adjustment is performed on the basis of interference sensitivity of OCT measurement. For example, the fine focus adjustment can be performed by: monitoring interference intensity (interference sensitivity) of interference signal acquired by performing OCT measurement of the subject's eye E; searching the position of the OCT focusing lens 43 so as to maximize the interference intensity; and moving the OCT focusing lens 43 to the searched position.

To perform the optical path length difference adjustment, the optical system is controlled so that a predetermined position on the subject's eye E is a reference position of a measurement range in the depth direction. This control is performed on at least one of the optical path length changing unit 41 and the reference driver 114A. Thereby, the difference of the optical path length between the measurement optical path and the reference optical path is adjusted. By setting the reference position in the optical path length difference adjustment, OCT measurement can be performed with high accuracy over a desired measurement range in the depth direction simply by changing the wavelength sweep speed.

To perform the polarization adjustment, the polarization state of the reference light LR is adjusted for optimizing the interference efficiency between the measurement light LS and the reference light LR.

(Storage Unit)

The storage unit 212 stores various types of data. Examples of the data stored in the storage unit 212 include image data of an OCT image, image data of a fundus image, image data of an anterior segment image, and subject's eye information. The subject's eye information includes information on the subject such as patient ID and name, and information on the subject's eye such as identification information of the left eye/right eye.

Further, scan control information 212A is stored in the storage unit 212. The scan control information 212A includes an execution order of a plurality of scans to be sequentially performed and setting information of each scan (B scan). The setting information of scan includes a size of the scan region, a position (for example, displacement from a predetermined scan center position) of the scan region, a scan mode, and the like. The main controller 211 can set a scan region having a predetermined size at a predetermined position for each scan, and can control to perform scan in a predetermined scan mode, by referring to the scan control information 212A. Examples of the scan mode include a radial scan, a line scan, a circle scan, and the like. In some embodiments, the size of the scan region and the scan mode are the same for the plurality of scans.

In some embodiments, the setting information of scan includes information corresponding to the measurement range in the depth direction. In this case, the main controller 211 can change the difference of the optical path lengths so as to be within a predetermined measurement range in the depth direction for each scan, and can control to perform OCT measurement, by referring to the scan control information 212A.

In addition, the storage unit 212 stores various kinds of computer programs and data for operating the ophthalmologic apparatus 1.

(Image Forming Unit)

The image forming unit 220 forms an OCT image of the subject's eye E based on the sampling data obtained by sampling the detection signal from the detector 125 using the DAQ 130. Examples of the OCT image formed by the image forming unit 220 include an A-scan image, a B-scan image (tomographic image), a C-scan image, and the like. As with the conventional swept source OCT, the image formation process includes noise removal (noise reduction), filtering, dispersion compensation, fast Fourier transform (FFT), and the like. In the case of employing an OCT apparatus of another type, the image forming unit 220 performs known processing according to the type employed.

The image forming unit 220 includes, for example, the circuitry described above. Note that "image data" and an "image" based on the image data may not be distinguished from each other in the present specification.

(Data Processor)

The data processor 230 processes data acquired through photography of the subject's eye E or data acquired through OCT measurement. For example, the data processor 230 performs various kinds of image processing and various kinds of analysis processing on the image formed by the image forming unit 220. For example, the data processor 230 performs various types of image correction such as brightness correction. The data processor 230 performs various kinds of image processing and various kinds of analysis on images captured by the fundus camera unit 2 (e.g., fundus images, anterior segment images, etc.).

The data processor 230 performs known image processing such as interpolation for interpolating pixels in tomographic images to form three-dimensional image data of the fundus Ef. Note that image data of a three-dimensional image means image data in which the position of a pixel is defined by a three-dimensional coordinate system. Examples of the image data of the three-dimensional image include image data defined by voxels three-dimensionally arranged. Such image data is referred to as volume data or voxel data. When displaying an image based on volume data, the data processor 230 performs rendering (volume rendering, maximum intensity projection (MIP), etc.) on the volume data, thereby forming image data of a pseudo three-dimensional image viewed from a particular line of sight. The pseudo three-dimensional image is displayed on the display device such as a display unit 240A.

The three-dimensional image data may be stack data of a plurality of tomographic images. The stack data is image data formed by three-dimensionally arranging tomographic images along a plurality of scan lines based on positional relationship of the scan lines. That is, the stack data is image data formed by representing tomographic images, which are originally defined in their respective two-dimensional coordinate systems, by a single three-dimensional coordinate system. That is, the stack data is image data formed by embedding tomographic images into a single three-dimensional space.

The data processor 230 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired three-dimensional data set (volume data, stack data, etc.). An image in an arbitrary cross section such as the B-mode image or the C-mode image is formed by selecting pixels (voxels) on a designated cross section from the three-dimensional data set. The projection image is formed by projecting the three-dimensional data set in a predetermined direction (Z direction, depth direction, axial direction). The shadowgram is formed by projecting a part of the three-dimensional data set (for example, partial data corresponding to a, specific layer) in a predetermined direction. An image having a viewpoint on the front side of the subject's eye, such as the C-mode image, the projection image, and the shadowgram, is called a front image (en-face image).

The data processor 230 can build (form) the B-mode image or the front image (blood vessel emphasized image, angiogram) in which retinal blood vessels and choroidal blood vessels are emphasized (highlighted), based on data (for example, B-scan image data) acquired in time series by OCT. For example, the OCT data in time series can be acquired by repeatedly scanning substantially the same site of the subject's eye E.

In some embodiments, the data processor 230 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 230 forms an OCTA image by extracting information of a predetermined thickness at a desired site from a plurality of built emphasized images and building as an en-face image.

An image (for example, a three-dimensional image, a B-mode image, a C-mode image, a projection image, a shadowgram, and an OCTA image) generated by the data processor 230 is also included in the OCT image.

As shown in FIG. 5, the data processor 230 includes an analyzer 231 and an image composing unit 232.

The analyzer 231 analyzes the detection result of the interference light obtained by performing OCT measurement to determine a focus state of the measurement light LS in the fine focus adjustment control. For example, the main controller 211 performs repetitive OCT measurements while controlling the focusing driver 43A according to a predetermined algorithm. The analyzer 231 analyzes detection results of interference light LC repeatedly acquired by performing OCT measurement to calculate a predetermined evaluation value relating to image quality of the OCT image. The analyzer 231 determines whether the calculated evaluation value is equal to or less than a threshold. In some embodiments, the fine focus adjustment is continued until the calculated evaluation value becomes equal to or less than the threshold. That is, when the evaluation value is equal to or less than the threshold, it is determined that the focus state of the measurement light LS is appropriate. And the fine focus adjustment is continued until it is determined that the focus state of the measurement light LS is appropriate.

In some embodiments, the main controller 211 monitors the intensity of the interference signal (interference intensity, interference sensitivity) acquired sequentially while acquiring the interference signal by performing the repetitive OCT measurements described above. In addition, while performing this monitoring process, the OCT focusing lens 43 is moved to find the position of the OCT focusing lens 43 in which the interference intensity is maximized. With the fine focus adjustment thus performed, the OCT focusing lens 43 can be guided to the position where the interference intensity is optimized.

Further, the analyzer 231 the detection result of the interference light obtained by performing OCT measurement to determine a polarization state of at least one of the measurement light LS and the reference light LR. For example, the main controller 211 performs repetitive OCT measurements while controlling at least one of the polarization controllers 103 and 118 according to a predetermined algorithm. In some embodiments, the main controller 211 controls the attenuator 120 to change an attenuation of the reference light LR. The analyzer 231 analyzes detection results of interference light LC repeatedly acquired by performing OCT measurement to calculate a predetermined evaluation value relating to image quality of the OCT image. The analyzer 231 determines whether the calculated evaluation value is equal to or less than a threshold. The threshold is set in advance. Polarization adjustment is continued until the evaluation value calculated becomes equal to or less than the threshold. That is, when the evaluation value is equal to or less than the threshold, it is determined that the polarization state of the measurement light LS is appropriate. And the polarization adjustment is continued until it is determined that the polarization state of the measurement light LS is appropriate.

In some embodiments, the main controller 211 can monitor the interference intensity also in the polarization adjustment.

Further, the analyzer 231 can specify a characteristic region by analyzing the detection result of the interference light acquired by performing OCT measurement or the OCT image formed based on the detection result. Examples of the characteristic region include a region including a characteristic site and a blood vessel. Examples of the characteristic site include a predetermined site, such as an optic disc, a fovea, and a macula, and a diseased site.

Further, the analyzer 231 performs predetermined analysis processing on the detection result of the interference light acquired by performing OCT measurement or the OCT image formed based on the detection result. Examples of the predetermined analysis processing include specifying (identification) of a predetermined site (tissue, lesion) of the subject's eye E; calculation of a distance between designated sites (distance between layers, interlayer distance), area, angle, ratio, or density; calculation by a designated formula; specifying of the shape of a predetermined site; calculation of these statistics; calculation of distribution of the measured value or the statistics; image processing based on these analysis processing results, and the like. Examples of the predetermined tissue include a blood vessel, an optic disc, a fovea, a macula, and the like. Examples of the predetermined lesion include a leukoma, a hemorrhage, and the like.

The image composing unit 232 generates a wide-angle OCT image by composing OCT images acquired by performing a plurality of OCT measurements. For example, the image composing unit 232 generates one wide-angle OCT image by composing a plurality of OCT images so that characteristic regions, which are common to the plurality of OCT images specified by the analyzer 231, overlap. The image composing unit 232 can generate one OCT image by performing known enlargement processing, known reduction processing, known rotation processing, or known deformation processing on at least one of the plurality of OCT images.

Further, the image composing unit 232 can compose the plurality of OCT images to generate a wide-angle OCT image, based on anatomical data of the eye, clinical data of the eye, or the like.

The data processor 230 that functions as described above includes, for example, the aforementioned microprocessor, RAM, ROM, hard disk drive, circuit board, and the like. Computer programs that cause a microprocessor to execute the above functions are previously stored in a storage device such as a hard disk drive.

(User Interface)

The user interface 240 includes the display unit 240A and an operation unit 240B. The display unit 240A includes the aforementioned display device of the arithmetic control unit 200 and the display apparatus 3. The operation unit 240B includes the aforementioned operation device of the arithmetic control unit 200. The operation unit 240B may include various types of buttons and keys provided on the case of the ophthalmologic apparatus 1 or the outside. For example, when the fundus camera unit 2 has a case similar to that of the conventional fundus camera, the operation unit 240B may include a joy stick, an operation panel, and the like provided to the case. Besides, the display unit 240A may include various types of display devices such as a touch panel and the like arranged on the case of the fundus camera unit 2.

Note that the display unit 240A and the operation unit 240B need not necessarily be formed as separate devices. For example, a device like a touch panel, which has a display function integrated with an operation function, can be used. In such cases, the operation unit 240B includes the touch panel and a computer program. The content of operation performed on the operation unit 240B is fed to the controller 210 in the morphology of an electrical signal. Moreover, operations and inputs of information may be performed by using a graphical user interface (GUI) displayed on the display unit 240A and the operation unit 240B.

The LCD 39 is an example of the "fixation projection system" according to the embodiments. The optical system included in the OCT unit 100 is an example of the "interference optical system" according to the embodiments. The optical path length changing unit 41, or the corner cube 114 and the reference driver 114A is an example of the "optical path difference changing unit" according to the embodiments. The DAQ 130 is an example of the "sampling unit" according to the embodiments. The image forming unit 220 or the data processor 230 is an example of the "image forming unit" according to the embodiments.

[Operation]

The operation of the ophthalmologic apparatus 1 according to the embodiments will be described.

The first operation example represents an operation example in the case of performing scan on the first scan region and the second scan region. However, the scan can be performed on three or more scan regions in the same manner.

FIG. 7 shows a first operation example of the ophthalmologic apparatus 1 according to the embodiments. FIG. 7 shows a flowchart of the first operation example of the ophthalmologic apparatus 1 according to the embodiments. The storage unit 212 stores computer programs for realizing the processing shown in FIG. 7. The main controller 211 operates according to the computer programs, and thereby the main controller 211 performs the processing shown in FIG. 7.

(S1: Perform Alignment)

The main controller 211 performs alignment. That is, the main controller 211 controls the alignment optical system 50 to project the alignment indicator onto the subject's eye E. At this time, a fixation target generated by the LCD 39 is also projected onto the subject's eye E. The main controller 211 controls the movement mechanism 150 based on the movement amount of the optical system to relatively to move the optical system with respect to the subject's eye E by the movement amount. The movement amount is specified based on the receiving light image obtained using the image sensor 35, for example. The main controller 211 repeatedly executes this processing.

In some embodiments, the alignment rough adjustment and the alignment fine adjustment described above are performed after the alignment in step S1 is completed.

(S2: Present Fixation Target)

Subsequently, the main controller 211 controls the LCD 39 to display a fixation target for OCT measurement at a predetermined position on the LCD 39. The main controller 211 can display the fixation target at a display position on the LCD 39 corresponding to a position of an optical axis of the optical axis on the fundus Ef.

(S3: Set Optical Scanner for First Scan Region)

The main controller 211 sets the size of the scan region, the position of the scan region, and the scan mode in the scan region for performing scan on the first scan region SCAN1 for the optical scanner 42. In some embodiments, the main controller 211 sets the size, and the like of the scan region, based on the scan control information 212A.

(S4: Acquire Tomographic Image for Adjustment)

Subsequently, the main controller 211 controls the OCT unit 100 to perform OCT provisional measurement, and to acquire a tomographic image for adjustment for adjusting the reference position of the measurement range in the depth direction. Specifically, the main controller 211 controls the optical scanner 42 to deflect the measurement light LS generated based on the light L0 emitted from the light source unit 101 and to scan a predetermined site (for example, fundus) of the subject's eye E with the deflected measurement light LS. The detection result of the interference light obtained by scanning with the measurement light LS is sent to the image forming unit 220 after being sampled in synchronization with the clock KC. The image forming unit 220 forms the tomographic image (OCT image) of the subject's eye E from the obtained interference signal.

(S5: Adjust Reference Position in Depth Direction)

Subsequently, the main controller 211 adjusts the reference position of the measurement range in the depth direction (z direction). For example, the main controller 211 controls the analyzer 231 to specify a predetermined site (for example, sclera) in the tomographic image obtained in step S4, and sets a position separated by a predetermined distance in the depth direction from the specified position of the predetermined site as the reference position of the measurement range. Alternatively, a predetermined position determined in advance so that the optical path lengths of the measurement light LS and the reference light LR substantially coincide may be set as the reference position of the measurement range.

(S6: Adjust Focusing, Adjust Polarization)

Next, the main controller 211 perform control of adjusting focusing and of adjusting polarization.

For example, the main controller 211 controls the OCT unit 100 to perform OCT measurement, after controlling the focusing driver 43A to move the OCT focusing lens 43 by a predetermined distance. The main controller 211 controls the analyzer 231 to determine the focus state of the measurement light LS based on the detection result of the interference light acquired by performing OCT measurement, as described above. When it is determined that the focus state is not appropriate based on the determination result obtained by the analyzer 231, the main controller 211 controls the focusing driver 43A again and repeats this until it is determined that the focus state of the measurement light LS is appropriate.

Further, for example, the main controller 211 controls the OCT unit 100 to perform OCT measurement after controlling at least one of the polarization controllers 103 and 118 to change the polarization state of at least one of the light L0 and the measurement light LS by a predetermined amount. And then, the main controller 211 controls the image forming unit 220 to form the OCT image on the basis of the acquired detection result of the interference light. The main controller 211 controls the analyzer 231 to determine the image quality of the OCT image acquired by performing OCT measurement, as described above. When it is determined that the polarization state is not appropriate based on the determination result obtained by the analyzer 231, the main controller 211 controls the polarization controllers 103 and 118 again and repeats this until it is determined that the polarization state of the measurement light LS is appropriate.

(S7: Acquire Interference Signal)

Subsequently, the main controller 211 controls the OCT unit 100 to perform OCT measurement. The detection result of the interference light acquired by the OCT measurement is sampled by the DAQ 130 and is stored as the interference signal in the storage unit 212 or the like.

(S8: Set Optical Scanner for Second Scan Region)

The main controller 211 sets the size of the scan region, the position of the scan region, and the scan mode in the scan region for performing scan on the second scan region SCAN2 for the optical scanner 42. In some embodiments, the main controller 211 sets the size, and the like of the scan region, based on the scan control information 212A.

(S9: Acquire Tomographic Image for Adjustment)

Subsequently, the main controller 211 controls the OCT unit 100 to perform OCT provisional measurement, and to acquire a tomographic image for adjustment for adjusting the reference position of the measurement range in the depth direction. In step S9, the fixation light flux is projected at the same projected position on the fundus Ef as in steps S4 and S7. Specifically, the main controller 211 controls the optical scanner 42 to deflect the measurement light LS generated based on the light L0 emitted from the light source unit 101 and to scan the predetermined site of the subject's eye E with the deflected measurement light LS, in the same manner as step S4. The detection result of the interference light obtained by scanning with the measurement light LS is sent to the image forming unit 220 after being sampled in synchronization with the clock KC. The image forming unit 220 forms the tomographic image (OCT image) of the subject's eye E from the obtained interference signal.

(S10: Adjust Reference Position in Depth Direction)

Subsequently, the main controller 211 adjusts the reference position of the measurement range in the depth direction (z direction). Specifically, the, the main controller 211 controls the analyzer 231 to specify a predetermined site in the tomographic image obtained in step S9, and sets a position separated by a predetermined distance in the depth direction from a position of the specified predetermined site as the reference position of the measurement range. In step S10, the reference position corresponding to the second scan region SCAN2 is set.

(S11: Adjust Focusing, Adjust Polarization)

Next, the main controller 211 performs control of adjusting focusing and of adjusting polarization, in the same manner as step S6.

(S12: Acquire Interference Signal)

Subsequently, the main controller 211 controls the OCT unit 100 to perform OCT measurement. The detection result of the interference light acquired by the OCT measurement is sampled by the DAQ 130 and is stored as the interference signal in the storage unit 212 or the like. In step S12, the fixation light flux is projected at the same projected position on the fundus Ef as in steps S4 and S7.

In case of performing scan on three or more scan regions, steps S8 to S12 are repeated.

(S13: Analyze Interference Signal•Form Tomographic Image)

Next, the main controller 211 controls the image forming unit 220 to form the OCT image of the subject's eye E based on the interference signal acquired in step S7. In the same manner, the main controller 211 controls the image forming unit 220 to form the OCT image of the subject's eye E based on the interference signal acquired in step S12. Further, the main controller 211 controls the analyzer 231 to perform predetermined analysis processing on the formed OCT image.

In some embodiments, the main controller 211 controls the analyzer 231 to perform predetermined analysis processing on at least one of the interference signal acquired in step S7 and the interference signal acquired in step S12.

(S14: Generate Wide-Angle OCT Image)

Next, the main controller 211 controls the analyzer 231 to specify a characteristic region in the two OCT images formed in step S13, and composes the two OCT images based on the specified characteristic region to generate a wide-angle OCT image.

This terminates the operation of the ophthalmologic apparatus 1 (END).

In the second operation example, the OCT measurement range is changed by changing the wavelength sweep speed for each scan.

FIG. 8 shows a second operation example of the ophthalmologic apparatus 1 according to the embodiments. FIG. 8 represents a flowchart of the second operation example according to the embodiments. The storage unit 212 stores computer programs for realizing the processing shown in FIG. 8. The main controller 211 operates according to the computer programs, and thereby the main controller 211 performs the processing shown in FIG. 8.

(S21: Perform Alignment)

The main controller 211 performs alignment, in the same manner as step S1.

(S22: Present Fixation Target)

Subsequently, the main controller 211 controls the LCD 39 to display the fixation target at a predetermined position on the LCD 39, in the same manner as step S2.

(S23: Set Optical Scanner for First Scan Region)

The main controller 211 sets the size of the scan region, the position of the scan region, and the scan mode in the scan region for performing scan on the first scan region SCAN1 for the optical scanner 42, in the same manner as step S3.

(S24: Set Wavelength Sweep Speed)

Next, the main controller 211 sets the wavelength sweep speed for the first scan region, for the light source 140 in the light source unit 101. Thereby, the light source 140 starts a predetermined wavelength range sweep at the set wavelength sweep speed. The optical selection output device 144 in the light source unit 101 selectively outputs the composed light from the MZI 143 corresponding to the set wavelength sweep speed. As a result, the frequency of the clock KC does not change.

(S25: Acquire Tomographic Image for Adjustment)

Subsequently, the main controller 211 controls the OCT unit 100 to perform OCT provisional measurement, and to acquire a tomographic image for adjustment for adjusting the reference position of the measurement range in the depth direction, in the same manner as step S4.

(S26: Adjust Reference Position in Depth Direction)

Subsequently, the main controller 211 adjusts the reference position of the measurement range in the depth direction (z direction), in the same manner as step S5.

(S27: Adjust Focusing, Adjust Polarization)

Next, the main controller 211 performs control of adjusting focusing and of adjusting polarization, in the same manner as step S6.

(S28: Acquire Interference Signal)

Subsequently, the main controller 211 controls the OCT unit 100 to perform OCT measurement, in the same manner as step S7. The detection result of the interference light acquired by the OCT measurement is sampled by the DAQ 130 and is stored as the interference signal in the storage unit 212 or the like.

(S29: Set Optical Scanner for Second Scan Region)

The main controller 211 sets the size of the scan region, the position of the scan region, and the scan mode in the scan region for performing scan on the second scan region SCAN2 for the optical scanner 42, in the same manner as step S8.

(S30: Set Wavelength Sweep Speed)

Next, the main controller 211 sets the wavelength sweep speed for the second scan region, for the light source 140 in the light source unit 101. Thereby, the light source 140 starts a predetermined wavelength range sweep at the set wavelength sweep speed. The optical selection output device 144 in the light source unit 101 selectively outputs the composed light from the MZI 143 corresponding to the set wavelength sweep speed. As a result, the frequency of the clock KC does not change.

(S31: Acquire Tomographic Image for Adjustment)

Subsequently, the main controller 211 controls the OCT unit 100 to perform OCT provisional measurement, and to acquire a tomographic image for adjustment for adjusting the reference position of the measurement range in the depth direction, in the same manner as step S9.

(S32: Adjust Reference Position in Depth Direction)

Subsequently, the main controller 211 adjusts the reference position of the measurement range in the depth direction (z direction), in the same manner as step S10.

(S33: Adjust Focusing, Adjust Polarization)

Next, the main controller 211 performs control of adjusting focusing and of adjusting polarization, in the same manner as step S27.

(S34: Acquire Interference Signal)

Subsequently, the main controller 211 controls the OCT unit 100 to perform OCT measurement, in the same manner as step S28. In step S34, the fixation light flux is projected at the same projected position on the fundus Ef as in steps S25 and S28.

(S35: Analyze Interference Signal•Form Tomographic Image)

Next, the main controller 211 controls the image forming unit 220 to form the OCT image of the subject's eye E based on the interference signal acquired in step S28. In the same manner, the main controller 211 controls the image forming unit 220 to form the OCT image of the subject's eye E based on the interference signal acquired in step S34. Further, the main controller 211 controls the analyzer 231 to perform predetermined analysis processing on the formed OCT image.

In some embodiments, the main controller 211 controls the analyzer 231 to perform predetermined analysis processing on at least one of the interference signal acquired in step S28 and the interference signal acquired in step S34.

(S36: Generate Wide-Angle OCT Image)

Next, the main controller 211 controls the analyzer 231 to specify a characteristic region in the two OCT images formed in step S35, and composes the two OCT images based on the specified characteristic region to generate a wide-angle OCT image.

This terminates the operation of the ophthalmologic apparatus 1 (END).

Modification Example

In the embodiments described above, the case has been described in which the ophthalmologic apparatus performs swept source OCT. However, the configuration of the ophthalmologic apparatus according to the embodiments is not limited thereto. For example, the ophthalmologic apparatus according to the embodiments may perform spectral domain OCT. Hereinafter, an ophthalmologic apparatus according to a modification example of the embodiments will be described focusing on differences from the embodiments.

The difference between the configuration of the ophthalmologic apparatus according to the modification example of the embodiments and the configuration of the ophthalmologic apparatus 1 according to the embodiment is that the OCT unit 100a is provided instead of the OCT unit 100 and that the arithmetic control unit 200a is provided instead of the arithmetic control unit 200.

Figure 9:
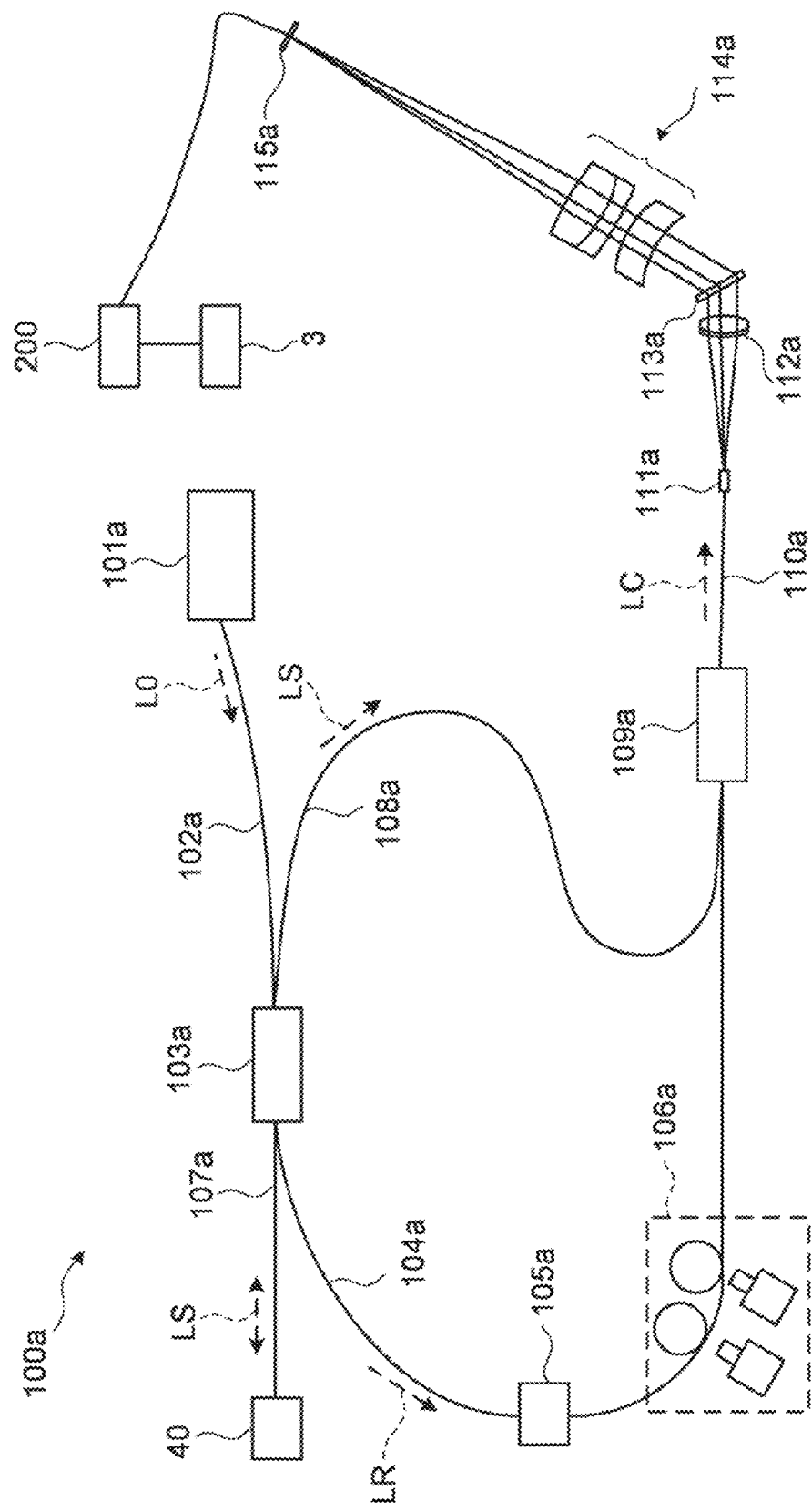
FIG. 9 is a schematic diagram illustrating an example of the configuration of the ophthalmologic apparatus according to a modification example of the embodiments.

FIG. 9 shows an example of the configuration of the OCT unit 100a according to the modification example of the embodiments. In FIG. 9, like reference numerals designate like parts as in FIG. 1. The same description may not be repeated.

The OCT unit 100a is provided with an optical system for performing spectral domain OCT. This optical system has a configuration similar to that of a conventional spectral domain type OCT apparatus. That is, this optical system is configured to: split low-coherence light into reference light and measurement light; make the measurement light returning from the fundus Ef and the reference light having traveled through the reference optical path interfere with each other to generate interference light; and detect spectral components of the interference light. This detection result (detection signal) is sent to the arithmetic control unit 200a.

A light source unit 101a includes a broadband light source and emits broadband, low-coherence light L0. The wavelength bands of the low-coherence light L0 includes, for example, near-infrared wavelengths (approximately 800 to 900 nm). The low-coherence light L0 has, for example, temporal coherence length of around several tens of micrometers. Note that, the low-coherence light L0 may be of wavelengths invisible for example human eyes, such as near-infrared light with a central wavelength of around 1040 to 1060 nm.

The light source unit 101a includes a light emission device, such as a super luminescent diode (SLD), an LED, a semiconductor optical amplifier (SOA), or the like.

The low coherence light L0 emitted from the light source unit 101a is guided to a fiber coupler 103a through an optical fiber 102a. The fiber coupler 103a splits the low coherence light L0 into measurement light LS and reference light LR.

The reference light LR is guided through an optical fiber 104a and arrives at an optical attenuator 105a. The attenuator 105a automatically adjusts the amount of the reference light LR guided through the optical fiber 104a under the control of the arithmetic control unit 200a using a known technology. The reference light LR whose light amount is adjusted by the attenuator 105a is guided to a polarization controller 106a through the optical fiber 104a, and the reference light LR arrives at the polarization controller 106a. The polarization controller 106a is a device that applies external stress to the looped optical the optical fiber 104a to thereby adjust the polarization state of the reference light LR guided through the optical the optical fiber 104a. Note that the configuration of the polarization controller 106a is not limited to this and any known technologies can be used. The reference light LR whose polarization state is adjusted by the polarization controller 106a arrives at a fiber coupler 109a.

The measurement light LS generated by the fiber coupler 103a is guided through an optical fiber 107a and is collimated into a parallel light beam by the collimator lens unit 40. Further, the measurement light LS reaches the dichroic mirror 46 via the optical path length changing unit 41, the optical scanner 42, the OCT focusing lens 43, the mirror 44, and the relay lens 45. Subsequently, the measurement light LS is reflected by the dichroic mirror 46, refracted by the objective lens 22, and projected onto the fundus Ef. The measurement light LS is scattered and reflected at various depth positions of the fundus Ef. Back-scattered light of the measurement light LS from the fundus Ef reversely advances along the same path as the outward path, and is guided to the fiber coupler 103a. Then, the back-scattered light passes through an optical fiber 108a, and arrives at a fiber coupler 109a.

The fiber coupler 109a makes the back-scattered light of the measurement light LS and the reference light LR having passed through fiber coupler 103a interfere with each other. The interference light LC thus generated is guided through an optical fiber 110a and is emitted from an emission end 111a. Further, the interference light LC is collimated into a parallel light beam by a collimator lens 112a, is spectrally divided (spectrally decomposed) by a diffraction grating 113a, is converged by a condenser lens 114a, and is projected onto the light receiving surface of a CCD image sensor 115a. Note that although FIG. 9 illustrates the diffraction grating 113a of the transmission type, it is possible to use a spectrally decomposing element of any other type, such as a diffraction grating of reflection type.

The CCD image sensor 115a is, for example, a line sensor. The CCD image sensor 115a detects the spectral components of the spectrally decomposed interference light LC, and converts the detected components into electric charges. The CCD image sensor 115a accumulates the electric charges to generate a detection signal, and sends the signal to the arithmetic control unit 200a.

Although a Michelson interferometer is employed in this embodiment, it is possible to employ any type of interferometer such as Mach-Zehnder-type as appropriate. In place of the CCD image sensor, an image sensor of other type, such as a complementary metal-oxide semiconductor (CMOS) image sensor, may be used.

Figure 10:
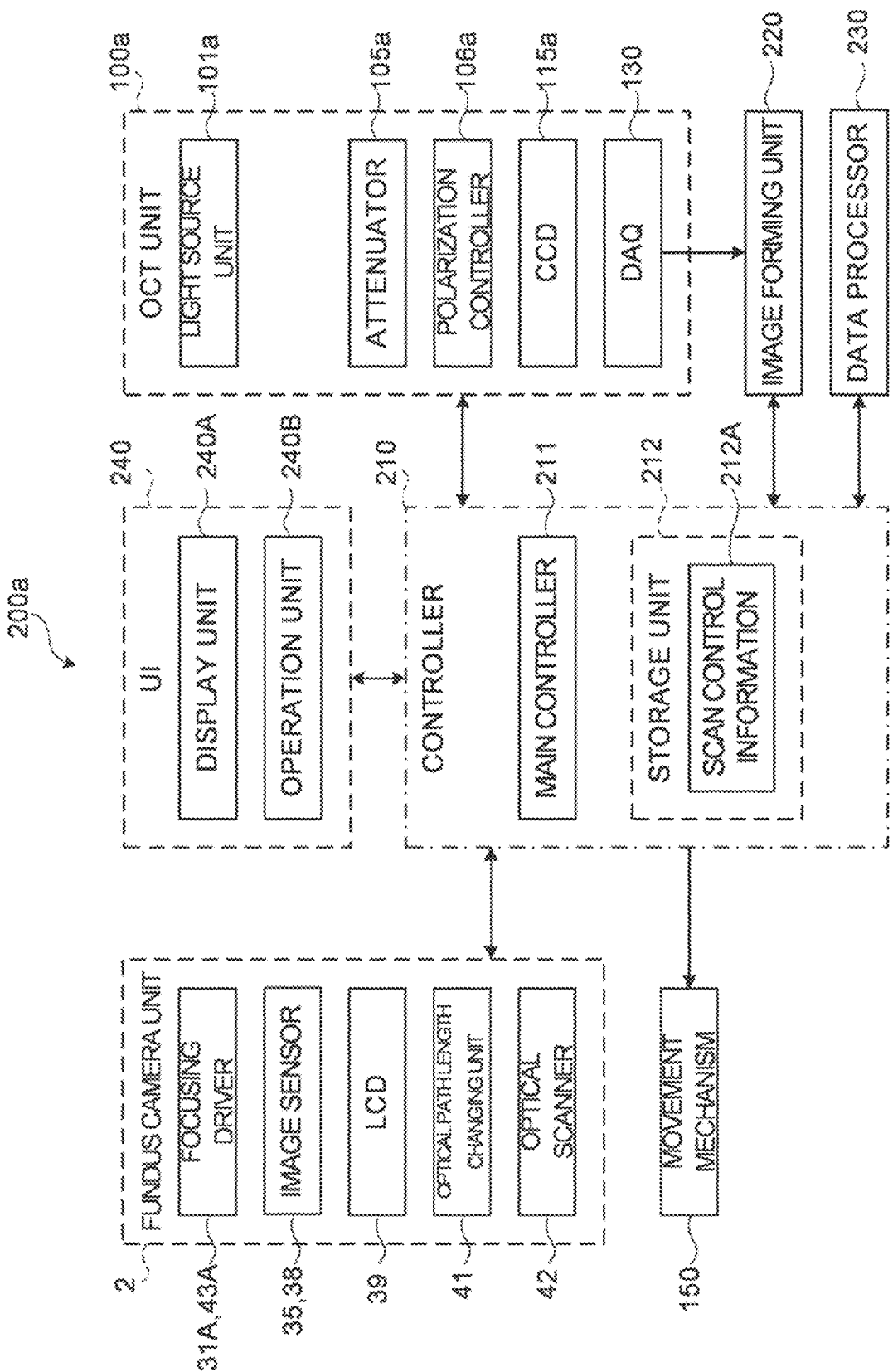
FIG. 10 is a schematic block diagram illustrating an example of the configuration of the ophthalmologic apparatus according to a modification example of the embodiments.

FIG. 10 shows a block diagram of an example of the configuration of the arithmetic control unit 200a according to the modification example of the embodiments. In FIG. 10, like reference numerals designate like parts as in FIG. 1, FIG. 4, or FIG. 9. The same description may not be repeated.

Similar to the arithmetic control unit 200 according to the embodiments, the arithmetic control unit 200a includes the controller 210, the image forming unit 220, and the data processor 230.

In the present modification example, the main controller 211 (controller 210) includes a processor and controls each part of the ophthalmologic apparatus according to the modification example of the embodiments. For example, the main controller 211 controls the components of the fundus camera unit 2, such as the optical path length changing unit 41, the optical scanner 42, the photography focusing lens 31 (focusing driver 31A), and the focus optical system 60, the OCT focusing lens 43 (focusing driver 43A), the image sensors 35 and 38, the LCD 39, and the entire optical system (movement mechanism 150), and the like. Further, the main controller 211 controls components of the OCT unit 100a, such as the light source unit 101a, the attenuator 105a, the polarization controller 106a, and the CCD image sensor 115a.

The operation of the ophthalmologic apparatus according to the modification example of the embodiments is the same as FIG. 6 and FIG. 7. Therefore, the detailed description is not repeated here. For example, in steps S6 and S11 in FIG. 7, the main controller 211 controls at least one of the polarization controllers 103 and 118 to change the polarization state of at least one of the light L0 and the measurement light LS. On the other hand, in the present modification example, the main controller 211 changes the polarization state of the reference light LR by controlling the polarization controller 106a.

According to the present modification example, as in the embodiments described above, wide-angle OCT measurement can be easily performed on the subject's eye in a short measurement time, compared with the case where the measurement site is moved by changing the projected position of the fixation target on the fundus to acquire the wide-angle OCT measurement result,

[Effects]

The ophthalmologic apparatus and the method of controlling the ophthalmologic apparatus according to the embodiments will be explained.

An ophthalmologic apparatus (1) according to some embodiments includes a fixation projection system (optical system including the LCD 39), an interference optical system (optical system included in the OCT unit 100), and a controller (210, main controller 211). The fixation projection system is configured to project fixation light flux onto a fundus (Ef) of a subject's eye (E). The interference optical system includes an optical scanner (42) and is configured to split light (L0) from light source (light source 140, light source unit 101a) into measurement light (LS) and reference light (LR), to irradiate the subject's eye with the measurement light deflected by the optical scanner, and to detect interference light (LC) between returning light of the measurement light from the subject's eye and the reference light. The controller is configured to perform OCT measurement on a first scan region (SCAN1) and a second scan region (SCAN2), which are different from each other in the subject's eye, by controlling the interference optical system in a state where a projected position of the fixation light flux on the fundus is fixed.

According to such a configuration, wide-angle OCT measurement can be easily performed on the subject's eye in a short measurement time, compared with the case where the measurement site is moved by changing the projected position of the fixation target on the fundus to acquire the wide-angle OCT measurement result, The ophthalmologic apparatus according to some embodiments further includes an optical path length difference changing unit (optical path length changing unit 41, or corner cube 114 and reference driver 114A) configured to change a difference of optical path lengths between an optical path of the measurement light and an optical path length of the reference light, wherein the controller is configured to change the difference of the optical path lengths by controlling the optical path length difference changing unit in accordance with a position of a scan region in the subject's eye, and to change a reference position of a measurement range in a depth direction of the OCT measurement on the subject's eye.

According to such a configuration, the reference position of the measurement range in the depth direction of the OCT measurement can be changed in accordance with the shape of the fundus. Thereby, wide-angle OCT measurement can be performed on the fundus.

In the ophthalmologic apparatus according to some embodiments, the controller is configured to change the difference of the optical path lengths when a distance between a scan center position of the first scan region and a scan center position of the second scan region is greater than a first distance.

According to such a configuration, it is not necessary to change the difference of the optical path length, in case that changing the position of the scan region within the measurement range in the depth direction determined by the optical system of the ophthalmologic apparatus. Thereby, the control of wide-angle OCT measurement can be simplified.

In the ophthalmologic apparatus according to some embodiments, in case that OCT measurement, in which a depth range is z0 millimeters and a scan length is L millimeters, is performed on the first scan region, the controller is configured to change the difference of the optical path lengths when the scan center position of the first scan region is arranged in a region separated by a predetermined distance (for example, 6 millimeters) or more from a predetermined site (macula, optic disc) of the subject's eye and L is greater than (2.5×z0).

According to such a configuration, the reference position of the measurement range in the depth direction of the OCT measurement can be changed in accordance with the shape of the fundus. Thereby, wide-angle OCT measurement can be performed on the fundus.

In the ophthalmologic apparatus according to some embodiments, the light source includes a wavelength sweep light source (light source 140) whose wavelength sweep speed can be changed, the ophthalmologic apparatus includes a sampling unit (DAQ 130) configured to sample detection result of the interference light at a predetermined sampling frequency, and the controller is configured to change the wavelength sweep speed by controlling the wavelength sweep light source in accordance with a position of a scan region in the subject's eye, and to change a depth range of the OCT measurement in the subject's eye.

According to such a configuration, the detection result of the interference light acquired by the interference optical system by changing the wavelength sweep speed is sampled at a predetermined sampling frequency. Thereby, the measurement range in the depth direction can be easily changed.

In the ophthalmologic apparatus according to some embodiments, in case that OCT measurement, in which a depth range is z0 millimeters and a scan length is L millimeters, is performed on the first scan region and a displacement in a scan direction of the scan center position of the second scan region with respect to the scan center position of the first scan region is d, the controller is configured to perform OCT measurement so that the depth range of the OCT measurement in the subject's eye is less than (z0+0.4×(d−L)) millimeters when d is greater than L.

According to such a configuration, the measurement range in the depth direction of the OCT measurement is changed in accordance with the shape of the fundus. Thereby, the ophthalmologic apparatus capable of easily performing wide-angle OCT measurement on the fundus can be provided.

The ophthalmologic apparatus according to some embodiments further includes an image forming unit (image forming unit 220 or data processor 230) configured to form an image of the subject's eye based on detection result of the interference light; and an image composing unit (232) configured to compose a first image formed by the image forming unit and a second image formed by the image forming unit, the first image being formed based on detection result of the interference light obtained by performing OCT measurement on the first scan region, the second image being formed based on detection result of the interference light obtained by performing OCT measurement on the second scan region.

According to such a configuration, the ophthalmologic apparatus capable of performing wide-angle OCT measurement on the subject's eye and of easily acquiring the wide-angle image of the subject's eye can be provided.

Some embodiments are methods of controlling the ophthalmologic apparatus including a fixation projection system (optical system including the LCD 39) and an interference optical system (optical system included in the OCT unit 100). The fixation projection system is configured to project fixation light flux onto a fundus (Ef) of a subject's eye (E). The interference optical system includes an optical scanner (42) and is configured to split light (L0) from light source (light source 140, light source unit 101*a*) into measurement light (LS) and reference light (LR), to irradiate the subject's eye with the measurement light deflected by the optical scanner, and to detect interference light (LC) between returning light of the measurement light from the subject's eye and the reference light. The method of controlling the ophthalmologic apparatus includes a first measurement step and a second measurement step. The first measurement step is performed to perform OCT measurement on a first scan region in the subject's eye by controlling the interference optical system, in a state where the fixation light flux is projected onto the fundus. The second measurement step is performed to perform OCT measurement on a second scan region in the subject's eye, the second scan region being different from the first scan region, by controlling the interference optical system, in a state where a fixation position in the first measurement step is fixed.

According to such a control, wide-angle OCT measurement can be easily performed on the subject's eye in a short measurement time, compared with the case where the measurement site is moved by changing the projected position of the fixation target on the fundus to acquire the wide-angle OCT measurement result, The method of controlling the ophthalmologic apparatus according to some embodiments further includes an optical path length difference changing step of changing a reference position of a measurement range in a depth direction of the OCT measurement on the subject's eye, by changing a difference of the optical path lengths between an optical path of the measurement light and an optical path of the reference light in accordance with a position of a scan region in the subject's eye.

According to such a control, the reference position of the measurement range in the depth direction of the OCT measurement can be changed in accordance with the shape of the fundus. Thereby, wide-angle OCT measurement can be performed on the fundus.

In the method of controlling the ophthalmologic apparatus according to some embodiments, the optical path length difference changing step is performed to change the difference of the optical path lengths when a distance between a scan center position of the first scan region and a scan center position of the second scan region is greater than a first distance.

According to such a control, it is not necessary to change the difference of the optical path length, in case that changing the position of the scan region within the measurement range in the depth direction determined by the optical system of the ophthalmologic apparatus. Thereby, the control of wide-angle OCT measurement can be simplified.

In the method of controlling the ophthalmologic apparatus according to some embodiments, in case that OCT measurement, in which a depth range is z0 millimeters and a scan length is L millimeters, is performed on the first scan region, the optical path length difference changing step is performed to change the difference of the optical path lengths when the scan center position of the first scan region is arranged in a region separated by a predetermined distance (for example, 6 millimeters) or more from a predetermined site (macula, optic disc) of the subject's eye and L is greater than (2.5×z0).

According to such a control, the reference position of the measurement range in the depth direction of the OCT measurement can be changed in accordance with the shape of the fundus. Thereby, wide-angle OCT measurement can be performed on the fundus.

In the method of controlling the ophthalmologic apparatus according to some embodiments, the light source includes a wavelength sweep light source (light source 140) whose wavelength sweep speed can be changed, the ophthalmologic apparatus includes a sampling unit (DAQ 130) configured to sample detection result of the interference light at a predetermined sampling frequency, and the method further includes a light source control step of changing the wavelength sweep speed by controlling the wavelength sweep light source in accordance with a position of a scan region in the subject's eye.

According to such a control, the detection result of the interference light acquired by the interference optical system by changing the wavelength sweep speed is sampled at a predetermined sampling frequency. Thereby, the measurement range in the depth direction can be easily changed.

In the method of controlling the ophthalmologic apparatus according to some embodiments, in case that OCT measurement, in which a depth range is z0 millimeters and a scan length is L millimeters, is performed on the first scan region and a displacement of the scan center position of the second scan region in a scan direction with respect to the scan center position of the first scan region is d, the second measurement step is performed to perform OCT measurement so that the depth range of the OCT measurement in the subject's eye is less than (z0+0.4×(d−L)) millimeters when d is greater than L.

According to such a control, the measurement range in the depth direction of the OCT measurement is changed in accordance with the shape of the fundus. Thereby, the ophthalmologic apparatus capable of easily performing wide-angle OCT measurement on the fundus can be provided.

The method of controlling the ophthalmologic apparatus according to some embodiments further includes an image forming step of forming an image of the subject's eye based on detection result of the interference light; and an image composing step of composing a first image formed in the image forming step and a second image formed in the image forming step, the first image being formed based on detection result of the interference light obtained by performing OCT measurement on the first scan region, the second image being formed based on detection result of the interference light obtained by performing OCT measurement on the second scan region.

According to such a control, wide-angle OCT measurement can be performed on the subject's eye and the wide-angle image of the subject's eye can be easily acquired.

In the above embodiment, the case where the detection result of the interference light in the wave number space is converted into the detection result of the interference light in the time space using the clock KC (that is, the k calibration method using the k clock) has been described. The configuration of the ophthalmologic apparatus 1 according to the embodiments is not limited to this. For example, the interference signal of MZI for k calibration may be acquired at the same time as the interference signal obtained by the OCT measurement, and the known k calibration processing may be performed by the data processor 230 to convert the interference signal in the wave number space into the interference signal in the time space.

A computer program for realizing the above embodiments can be stored in any kind of computer-readable recording medium. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like.

The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
a fixation projection system configured to project fixation light flux onto a fundus of a subject's eye;
an interference optical system including an optical scanner and configured to split light from light source into measurement light and reference light, to irradiate the subject's eye with the measurement light deflected by the optical scanner, and to detect interference light between returning light of the measurement light from the subject's eye and the reference light;
a controller configured to perform OCT measurement on a first scan region and a second scan region, which are different from each other in the subject's eye, by controlling the interference optical system in a state where a projected position of the fixation light flux on the fundus is fixed: and
an optical path length difference changing unit configured to change a difference of optical path lengths between an optical path of the measurement light and an optical path length of the reference light, wherein
the controller is configured to change the difference of the optical path lengths by controlling the optical path length difference changing unit in accordance with a position of a scan region in the subject's eye, and to change a reference position of a measurement range in a depth direction of the OCT measurement on the subject's eye.

2. The ophthalmologic apparatus of claim 1, wherein the controller is configured to change the difference of the optical path lengths when a distance between a scan center position of the first scan region and a scan center position of the second scan region is greater than a first distance.

3. The ophthalmologic apparatus of claim 1, wherein in case that OCT measurement, in which a depth range, is z0 millimeters and a scan length is L millimeters, is performed on the first scan region, the controller is configured to change the difference of the optical path lengths when the scan center position of the first scan region is arranged in a region separated by a predetermined distance or more from a predetermined site of the subject's eye and L is greater than (2.5×z0) millimeters.

4. The ophthalmologic apparatus of claim 2, further comprising
an image forming unit configured to form an image of the subject's eye based on detection result of the interference light; and
an image composing unit configured to compose a first image formed by the image forming unit and a second image formed by the image forming unit, the first image being formed based on detection result of the interference light obtained by perfoi ming OCT measurement on the first scan region, the second image being formed based on detection result of the interference light obtained by performing OCT measurement on the second scan region.

5. An ophthalmologic apparatus comprising:
a fixation projection system configured to project fixation light flux onto a fundus of a subject's eye:,
an interference optical system including an optical scanner and configured to split light from light source into measurement light and reference light, to irradiate the subject's eye with the measurement light deflected by the optical scanner, and to detect interference light between returning light of the measurement light from the subject's eye and the reference light; and
a controller configured to perform OCT measurement on a first scan region and a second scan region, which are different from each other in the subject's eye. by controlling the interference optical system in a state where a projected position of the fixation light flux on the fundus is fixed, wherein
the light source includes a wavelength sweep light source whose wavelength sweep speed can be changed,
the ophthalmologic apparatus includes a sampling unit configured to sample detection result of the interference light at a predetermined sampling frequency, and
the controller is configured to change the wavelength sweep speed by controlling the wavelength sweep light source in accordance with a position of a scan region in the subject's eye, and to change a depth range of the OCT measurement in the subject's eye.

6. An ophthalmologic apparatus comprising:
a fixation projection system configured to project fixation light flux onto a fundus of a subject's eye;
an interference optical system including an optical scanner and configured to split light from light source into measurement light and reference light, to irradiate the subject's eye with the measurement light deflected by the optical scanner, and to detect interference light between returning light of the measurement light from the subject's eye and the reference light: and
a controller configured to perform OCT measurement on a first scan region and a second scan region, which are different from each other in the subject's eye. by controlling the interference optical system in a state where a projected position of the fixation light flux on the fundus is fixed, wherein
in case that OCT measurement, in which a depth range is z0 millimeters and a scan length is L millimeters, is performed on the first scan region and a displacement in a scan direction of the scan center position of the second scan region with respect to the scan center position of the first scan region is d,
the controller is configured to perform OCT measurement so that the depth range of the OCT measurement in the subject's eye is less than (z0+0.4×(d−L)) millimeters when d is greater than L.

7. A method of controlling an ophthalmologic apparatus comprising;
a fixation projection system configured to project fixation light flux onto a fundus of a subject's eye; and
an interference optical system including an optical scanner and configured to split light from light source into measurement light and reference light, to irradiate the subject's eye with the measurement light deflected by the optical scanner, and to detect interference light between returning light of the measurement light from the subject's eye and the reference light, the method comprising:
a first measurement step of performing OCT measurement on a first scan region in the subject's eye by controlling the interference optical system, in a state where the fixation light flux is projected onto the fundus: and
a second measurement step of performing OCT measurement on a second scan region in the subject's eye, the second scan region being different from the first scan region, by controlling the interference optical system, in a state where a fixation position in the first measurement step is fixed, the method further comprising an optical path length difference changing step of changing a reference position of a measurement range in a depth direction of the OCT measurement on the subject's eye, by changing a difference of the optical path lengths between an optical path of the measurement light and an optical path of the reference light in accordance with a position of a scan region in the subject's eye.

8. The method of controlling the ophthalmologic apparatus of claim 7, wherein
the optical path length difference changing step is performed to change the difference of the optical path lengths when a distance between a scan center position of the first scan region and a scan center position of the second scan region is greater than a first distance.

9. The method of controlling the ophthalmologic apparatus of claim 7, wherein
in case that OCT measurement, in which a depth range, is z0 millimeters and a scan length is L millimeters, is performed on the first scan region,
the optical path length difference changing step is performed to change the difference of the optical path lengths when the scan center position of the first scan region is arranged in a region separated by a predetermined distance or more from a predetermined site of the subject's eye and L is greater than (2.5×z0) millimeters.

10. The method of controlling the ophthalmologic apparatus of claim 7, further comprising
an image forming step of forming an image of the subject's eye based on detection result of the interference light; and
an image composing step of composing a first image formed in the imaue forming step and a second image formed in the image forming step, the first image being formed based on detection result of the interference light obtained by performing OCT measurement on the first scan region, the second image being formed based on detection result of the interference light obtained by performing OCT measurement on the second scan region.

11. A method of controlling an ophthalmologic apparatus comprising:
a fixation projection system configured to project fixation light flux onto a fundus of a subject's eye; and
an interference optical system including an optical scanner and configured to split light from light source into measurement light and reference light, to irradiate the subject's eye with the measurement light deflected by the optical scanner, and to detect interference light between returning light of the measurement light from the subject's eye and the reference light, the method comprising:
a first measurement step of performing OCT measurement on a first scan region in the subject's eye by controlling the interference optical system, in a state where the fixation light flux is projected onto the fundus: and
a second measurement step of performing OCT measurement on a second scan region in the subject's eye, the second scan region being different from the first scan region, by controlling the interference optical system in a state where a fixation position in the first measurement step is fixed wherein
the light source includes a wavelength sweep light source whose wavelength sweep speed can be changed,
the ophthalmologic apparatus includes a sampling unit configured to sample detection result of the interference light at a predetermined sampling frequency, and
the method further comprises a light source control step of changing the wavelength sweep speed by controlling the wavelength sweep light source in accordance with a position of a scan region in the subject's eye.

12. A method of controlling an ophthalmologic apparatus comprising:
a fixation projection system configured to project fixation light flux onto a fundus of a subject's eye; and
an interference optical system including an optical scanner and configured to split light from light source into measurement light and reference light, to irradiate the subject's eye with the measurement light deflected by the optical scanner, and to detect interference light between returning light of the measurement light from the subject's eye and the reference light, the method comprising:
a first measurement step of performing OCT measurement on a first scan region in the subject's eye by controlling the interference optical system, in a state where the fixation light flux is projected onto the fundus; and
a second measurement step of performing OCT measurement on a second scan region in the subject's eye, the second scan region being different from the first scan region, by controlling the interference optical system, in a state where a fixation position in the first measurement step is fixed, wherein
in case that OCT measurement, in which a depth range is z0 millimeters and a scan length is L millimeters, is performed on the first scan region and a displacement of the scan center position of the second scan region in a scan direction with respect to the scan center position of the first scan region is d,
the second measurement step is performed to perform OCT measurement so that the depth range of the OCT measurement in the subject's eye is less than $(z0+0.4\times(d-L))$ millimeters when d is greater than L.

* * * * *